(12) United States Patent
Yagi et al.

(10) Patent No.: US 8,890,122 B2
(45) Date of Patent: Nov. 18, 2014

(54) ORGANIC ELECTROLUMINESCENT DEVICE

(75) Inventors: Kazunari Yagi, Ashigarakami-gun (JP); Ryo Nishio, Ashigarakami-gun (JP)

(73) Assignee: UDC Ireland Limited, Dublin (IE)

(*) Notice: Subject to any disclaimer, the term of this patent is extended or adjusted under 35 U.S.C. 154(b) by 968 days.

(21) Appl. No.: 12/532,880

(22) PCT Filed: Mar. 26, 2008

(86) PCT No.: PCT/JP2008/056533
§ 371 (c)(1),
(2), (4) Date: Sep. 24, 2009

(87) PCT Pub. No.: WO2008/123540
PCT Pub. Date: Oct. 16, 2008

(65) Prior Publication Data
US 2010/0108995 A1   May 6, 2010

(30) Foreign Application Priority Data

Mar. 30, 2007 (JP) ................................. 2007-094373

(51) Int. Cl.
| | | |
|---|---|---|
| H01L 29/08 | (2006.01) | |
| C09K 11/06 | (2006.01) | |
| C07D 209/40 | (2006.01) | |
| H01L 51/50 | (2006.01) | |
| C07D 209/08 | (2006.01) | |
| H01L 51/00 | (2006.01) | |

(52) U.S. Cl.
CPC ............ *H01L 51/5036* (2013.01); *C09K 11/06* (2013.01); *H01L 51/0085* (2013.01); *H01L 51/0072* (2013.01); *C07D 209/40* (2013.01); *C09K 2211/1029* (2013.01); *H01L 2251/552* (2013.01); *C07D 209/08* (2013.01)
USPC ................................ 257/40; 438/99; 313/504

(58) Field of Classification Search
USPC ................................ 257/40; 313/504; 438/99
See application file for complete search history.

(56) References Cited

U.S. PATENT DOCUMENTS

| | | | | |
|---|---|---|---|---|
| 6,670,053 | B2 * | 12/2003 | Conley | ......................... 428/690 |
| 6,815,093 | B2 | 11/2004 | Lin | |
| 2002/0117662 | A1 | 8/2002 | Nii | |
| 2003/0165712 | A1 | 9/2003 | Lin et al. | |
| 2004/0013903 | A1 | 1/2004 | Lin | |
| 2004/0135167 | A1 | 7/2004 | Nii | |
| 2004/0137262 | A1 | 7/2004 | Lin | |
| 2005/0249976 | A1 * | 11/2005 | Iwakuma et al. | ............. 428/690 |

FOREIGN PATENT DOCUMENTS

| | | |
|---|---|---|
| CN | 1562999 A | 1/2005 |
| CN | 1840525 A | 10/2006 |
| EP | 0 674 217 A1 | 9/1995 |
| EP | 1 339 264 A2 | 8/2003 |
| JP | 8-142502 A | 6/1996 |
| JP | 2001-123153 A | 5/2001 |
| JP | 2001-247859 A | 9/2001 |
| JP | 2002-15871 A | 1/2002 |
| JP | 2002-305084 A | 10/2002 |
| JP | 2003-277744 A | 10/2003 |
| JP | 2006-240102 A | 9/2006 |
| WO | 2004/108857 A1 | 12/2004 |

OTHER PUBLICATIONS

Ning, Z., et al. "Bisindolylmaleimide Derivatives as Non-Doped Red Organic Light-Emitting Materials." J. Photochem. & Photobio. A: Chem., vol. 192 (May 3, 2007): pp. 8-16.*
Yen, Tzu-San et al., "Electroluminescence of Bisindolylmaleimide Derivatives Containing Pentafluorophenyl Substituents", Chemistry of Materials, 2006, pp. 832-839, vol. 18, No. 3, American Chemical Society, XP-002484964.
Chiu, Ching-Wen et al., "Bisindolylmaleimides as Red Electroluminescence Materials", Chemistry of Materials, 2003, pp. 4527-4532, vol. 15, No. 23, American Chemical Society, XP-002484965.
International Search Report for PCT/JP2008/056533 date Oct. 30, 2008 [PCT/ISA/210].
Written Opinion PCT/JP2008/056533 [PCT/ISA/237].
Invitation to Pay Additional Fees for PCT/JP2008/056533 [PCT/ISA/206]—see pp. 2-3 re claims.
Office Action issued Mar. 21, 2012 in corresponding Chinese Application No. 200880010648.X.

* cited by examiner

*Primary Examiner* — Mark Tornow
(74) *Attorney, Agent, or Firm* — Riverside Law LLP

(57) ABSTRACT

An organic electroluminescent device is provided and includes: a pair of electrodes; and at least one organic layer between the pair of electrodes, the at least one organic layer including a light-emitting layer. The at least one organic layer contains an indole compound represented by formula (1):

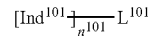

in which $Ind^{101}$ represents a substituted or unsubstituted indole ring, $L^{101}$ represents a linking group, $Ind^{101}$ and $L^{101}$ are connected to each other at 2- or 3-position of $Ind^{101}$, and $n^{101}$ represents an integer of 2 or more.

7 Claims, No Drawings

ORGANIC ELECTROLUMINESCENT DEVICE

TECHNICAL FIELD

The present invention relates to a light-emitting device, particularly an organic electroluminescent device (hereinafter also referred to as "light-emitting device" or "EL device"), capable of emitting light by converting electric energy into light.

BACKGROUND ART

Organic electroluminescent devices are attracting public attention as promising display devices for capable of emitting light of high luminance with low voltage. An important characteristic of organic electroluminescent devices is consumed electric power. Consumed electric power is equal to the product of the voltage and the electric current, and the lower the value of voltage that is necessary to obtain desired brightness and the smaller the value of electric current, the lower is the consumed electric power of the device.

As one attempt to lower the value of electric current that flows to a device, a light-emitting device utilizing luminescence from ortho-metalated iridium complex (Ir(ppy)$_3$: Tris-Ortho-Metalated Complex of Iridium(III) with 2-Phenylpyridine) is reported (see JPA-2001-247859). The phosphorescent devices disclosed therein are greatly improved in external quantum efficiency as compared with singlet luminescent devices in the related art, and have succeeded in making the value of electric current smaller. For the purpose of more enhancing efficiency and more improving durability of the phosphorescence device, devices containing a platinum complex having a tetradentate ligand have been reported (see WO 2004/108857).

On the other hand, for the purpose of improving luminance and efficiency, light-emitting devices using an indole derivative as a host material have also been reported (see, for example, JP-A-2002-305084 and JP-A-2003-277744). These light-emitting devices have succeeded in improving efficiency thereof, but more improvement has been desired in view of durability, reduction in driving voltage, and more enhancement of efficiency.

DISCLOSURE OF THE INVENTION

An object of the invention is to provide an organic electroluminescent device which has good durability and good luminance efficiency.

As a result of intensively searching for compounds capable of improving both durability and luminance efficiency, the inventors has found that compounds, in wherein indole rings are connected (including coordination bond), at 2- or 3 position of the indole ring, to a host group, exhibit remarkable effects with respect to an object of the invention. As a result of intensive investigation based on the knowledge, it has been found that an object of the invention can be attained by the following means.

(1) An organic electroluminescent device comprising:
a pair of electrodes; and
at least one organic layer between the pair of electrodes, the at least one organic layer including a light-emitting layer,
wherein the at least one organic layer contains an indole compound represented by formula (1):

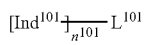

wherein $Ind^{101}$ represents a substituted or unsubstituted indole ring, $L^{101}$ represents a linking group, $Ind^{101}$ and $L^{101}$ are connected to each other at 2- or 3-position of $Ind^{101}$, and $n^{101}$ represents an integer of 2 or more.

(2) The organic electroluminescent device as described in item (1), wherein the indole compound represented by formula (1) is a compound represented by formula (2):

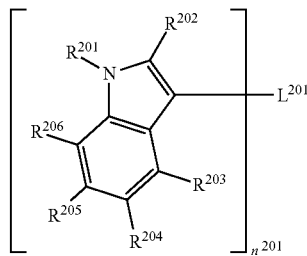

wherein $R^{201}$ to $R^{206}$ each represents a hydrogen atom or a substituent, $L^{201}$ represents a linking group, and $n^{201}$ represents an integer of 2 or more.

(3) An organic electroluminescent device comprising:
a pair of electrodes; and
at least one organic layer between the pair of electrodes, the at least one organic layer including a light-emitting layer,
wherein the at least one organic layer contains an indole compound represented by formula (3):

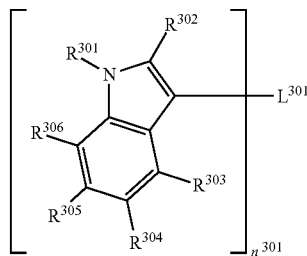

wherein $R^{301}$ to $R^{306}$ each represents a hydrogen atom or a substituent, $L^{301}$ represents a substituted or unsubstituted atom, and $n^{301}$ represents an integer of 2 or more.

(4) The organic electroluminescent device as described in any one of items (1) to (3) above, wherein the linking group is an alkyl liking group.

(5) The organic electroluminescent device as described in any one of items (1) to (4) above, wherein the substituent connected to the nitrogen atom of the indole ring is an aryl group.

(6) The organic electroluminescent device as described in any one of items (1) to (5) above, wherein the at least one organic layer contains a platinum complex having a tetradentate ligand.

(7) The organic electroluminescent device as described in any one of items (1) to (6) above, wherein the platinum complex is a compound represented by one of formulae (A), (C) and (D):

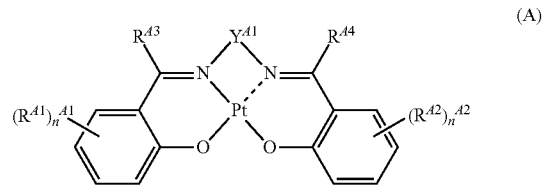

wherein $R^{A3}$ and $R^{A4}$ each independently represents a hydrogen atom or a substituent; and $R^{A1}$ and $R^{A2}$ each independently represents a substituent, and a plurality of $R^{A1}$'s and $R^{42}$s are present, the plurality of $R^{41}$s and $R^{42}$s may be the same or different and may be connected to each other to form a ring; $n^{41}$ and $n^{42}$ each independently represents an integer of from 0 to 4; and $Y^{41}$ represents a linking group,

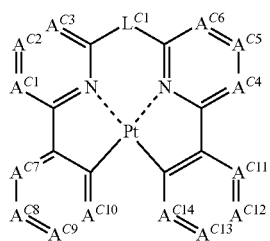
(C)

wherein $A^{C1}$ to $A^{C14}$ each independently represents C—R or N, and R represents a hydrogen atom or a substituent; and $L^{C1}$ represents a single bond or a divalent linking group, and

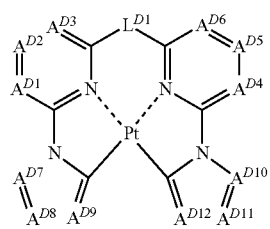
(D)

wherein $A^{D1}$ to $A^{D12}$ each independently represents C—R or N, and R represents a hydrogen atom or a substituent; and $L^{D1}$ represents a single bond or a divalent linking group.

(8) The organic electroluminescent device as described in any one of items (1) to (7) above, wherein the light-emitting layer contains at least one indole compound represented by any one of formulae (1) to (3).

(9) The organic electroluminescent device as described in any one of items (1) to (8) above, wherein the at least one indole compound includes an electron transporting layer containing a metal complex material.

(10) An indole compound represented by formula (4):

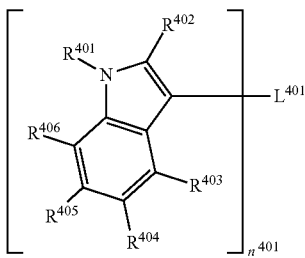

wherein $R^{401}$ represents a substituent, $R^{402}$ to $R^{406}$ each represents a hydrogen atom or a substituent, $L^{401}$ represents a substituted or unsubstituted atom or a group of atoms, and $n^{401}$ represents an integer of 2 or more.

Advantageous Effects

An organic electroluminescent device of the invention using the indole compound has realized both improvement of luminance efficiency and prolonging of life, and reduction of driving voltage.

In particular, compounds to be used in the invention in which indole rings are connected (including coordination bond), at 2- or 3 position of the indole ring, to a center element or elements, have more excellent luminance efficiency and life than those disclosed in JP-A-2002-305084 or JP-A-2003-277744 in which the rings are connected at 1-position of the indole ring.

Best Mode for Carrying Out the Invention

An organic electroluminescent device according to an exemplary embodiment of the invention is an organic electroluminescent device including a pair of electrodes and at least one organic layer between the pair of electrodes, the at least one organic layer including a light-emitting layer. The organic layer is a layer containing an organic compound, and the layer may be a layer containing an organic compound alone or may be a layer containing an inorganic compound in addition to the organic compound. Any layers in organic layers between the pair of electrodes can contain the compound represented by the above formula (1). Preferred embodiments of formula (1) are the above formulae (2), (3) and (4).

Formula (1) will be described below.

$Ind^{101}$ represents a substituted or unsubstituted indole ring. The examples of the substituents in $Ind^{101}$ include an alkyl group (preferably having from 1 to 30 carbon atoms, more preferably from 1 to 20 carbon atoms, and especially preferably from 1 to 10 carbon atoms, e.g., methyl, ethyl, isopropyl, tert-butyl, n-octyl, n-decyl, n-hexadecyl, cyclopropyl, cyclopentyl, cyclohexyl, etc., are exemplified), an alkenyl group (preferably having from 2 to 30 carbon atoms, more preferably from 2 to 20 carbon atoms, and especially preferably from 2 to 10 carbon atoms, e.g., vinyl, allyl, 2-butenyl, 3-pentenyl, etc., are exemplified), an alkynyl group (preferably having from 2 to 30 carbon atoms, more preferably from 2 to 20 carbon atoms, and especially preferably from 2 to 10 carbon atoms, e.g., propargyl, 3-pentynyl, etc., are exemplified), an aryl group (preferably having from 6 to 30 carbon atoms, more preferably from 6 to 20 carbon atoms, and especially preferably from 6 to 12 carbon atoms, e.g., phenyl, p-methylphenyl, naphthyl, anthranyl, etc., are exemplified), an amino group (preferably having from 0 to 30 carbon atoms, more preferably from 0 to 20 carbon atoms, and especially preferably from 0 to 10 carbon atoms, e.g., amino, methylamino, dimethylamino, diethylamino, dibenzylamino, diphenylamino, ditolylamino, etc., are exemplified), an alkoxyl group (preferably having from 1 to 30 carbon atoms, more preferably from 1 to 20 carbon atoms, and especially preferably from 1 to 10 carbon atoms, e.g., methoxy, ethoxy, butoxy, 2-ethylhexyloxy, etc., are exemplified), an aryloxy group (preferably having from 6 to 30 carbon atoms, more preferably from 6 to 20 carbon atoms, and especially preferably from 6 to 12 carbon atoms, e.g., phenyloxy, 1-naphthyloxy, 2-naphthyloxy, etc., are exemplified), a heterocyclic oxy group (preferably having from 1 to 30 carbon atoms, more preferably from 1 to 20 carbon atoms, and especially preferably from 1 to 12 carbon atoms, e.g., pyridyloxy, pyrazyloxy, pyrimidyloxy, quinolyloxy, etc., are exemplified), an acyl group (preferably having from 1 to 30 carbon atoms, more preferably from 1 to 20 carbon atoms, and especially preferably from 1 to 12 carbon atoms, e.g., acetyl, benzoyl, formyl, pivaloyl, etc., are exemplified), an alkoxycarbonyl group (preferably having from 2 to 30 carbon atoms, more preferably from 2 to 20 carbon atoms, and especially preferably from 2 to 12 carbon atoms, e.g., methoxycarbonyl, ethoxycarbonyl, etc., are exemplified), an aryloxycarbonyl group (preferably having from 7 to 30 carbon atoms, more preferably from 7 to 20 carbon atoms, and especially preferably from 7 to 12 carbon atoms, e.g., phenyloxycarbonyl, etc., are exemplified), an acyloxy group (preferably having from 2 to 30 carbon atoms, more preferably from 2 to 20 carbon atoms, and especially preferably from 2 to 10 carbon atoms, e.g., acetoxy, benzoyloxy, etc., are exemplified), an acylamino group (preferably having from 2 to 30 carbon atoms, more preferably from 2 to 20 carbon atoms, and especially preferably from 2 to 10 carbon atoms, e.g., acetylamino, benzoylamino, etc., are exemplified), an alkoxycarbonylamino group (preferably having from 2 to 30 carbon atoms, more preferably from 2 to 20 carbon atoms, and especially preferably from 2 to 12 carbon atoms, e.g., methoxycarbonylamino, etc., are exemplified), an aryloxycarbonylamino group (preferably having from 7 to 30 carbon atoms, more preferably from 7 to 20 carbon atoms, and especially preferably from 7 to 12 carbon atoms, e.g., phenyloxycarbonylamino, etc., are exemplified), a sulfonylamino group (preferably having from 1 to 30 carbon atoms, more preferably from 1 to 20 carbon atoms, and especially preferably from 1 to 12 carbon atoms, e.g., methanesulfonylamino, benzenesulfonylamino, etc., are exemplified), a sulfamoyl group (preferably having from 0 to 30 carbon atoms, more preferably from 0 to 20 carbon atoms, and especially preferably from 0 to 12 carbon atoms, e.g., sulfamoyl, methylsulfamoyl, dimethylsulfamoyl, phenylsulfamoyl, etc., are exemplified), a carbamoyl group (preferably having from 1 to 30 carbon atoms, more preferably from 1 to 20 carbon atoms, and especially preferably from 1 to 12 carbon atoms, e.g., carbamoyl, methylcarbamoyl, diethylcarbamoyl, phenylcarbamoyl, etc., are exemplified), an alkylthio group (preferably having from 1 to 30 carbon atoms, more preferably from 1 to 20 carbon atoms, and especially preferably from 1 to 12 carbon atoms, e.g., methylthio, ethylthio, etc., are exemplified), an arylthio group (preferably having from 6 to 30 carbon atoms, more preferably from 6 to 20 carbon atoms, and especially preferably from 6 to 12 carbon atoms, e.g., phenylthio, etc., are exemplified), a heterocyclic thio group (preferably having from 1 to 30 carbon atoms, more preferably from 1 to 20 carbon atoms, and especially preferably from 1 to 12 carbon atoms, e.g., pyridylthio, 2-benzimizolylthio, 2-benzoxazolylthio, 2-benzothiazolylthio, etc., are exemplified), a sulfonyl group (preferably having from 1 to 30 carbon atoms, more preferably from 1 to 20 carbon atoms, and especially preferably from 1 to 12 carbon atoms, e.g., mesyl, tosyl, etc., are exemplified), a sulfinyl group (preferably having from 1 to 30 carbon atoms, more preferably from 1 to 20 carbon atoms, and especially preferably from 1 to 12 carbon atoms, e.g., methanesulfinyl, benzenesulfinyl, etc., are exemplified), a ureido group (preferably having from 1 to 30 carbon atoms, more preferably from 1 to 20 carbon atoms, and especially preferably from 1 to 12 carbon atoms, e.g., ureido, methylureido, phenylureido, etc., are exemplified), a phosphoric amido group (preferably having from 1 to 30 carbon atoms, more preferably from 1 to 20 carbon atoms, and especially preferably from 1 to 12 carbon atoms, e.g., diethylphosphoric amido, phenylphosphoric amido, etc., are exemplified), a hydroxyl group, a mercapto group, a halogen atom (e.g., a fluorine atom, a chlorine atom, a bromine atom, an iodine atom), a cyano group, a sulfo group, a carboxyl group, a nitro group, a hydroxamic acid group, a sulfino group, a hydrazino group, an imino group, a heterocyclic group (preferably having from 1 to 30 carbon atoms, and more preferably from 1 to 12 carbon atoms, and as the hetero atoms, e.g., a nitrogen atom, an oxygen atom, a sulfur atom are exemplified, specifically, e.g., imidazolyl, pyridyl quinolyl, furyl, thienyl, piperidyl, morpholino, benzoxazolyl, benzimidazolyl, benzothiazolyl, carbazolyl, azepinyl, etc., are exemplified), a silyl group (preferably having from 3 to 40 carbon atoms, more preferably from 3 to 30 carbon atoms, and especially preferably from 3 to 24 carbon atoms, e.g., trimethylsilyl, triphenylsilyl, etc., are exemplified), a silyloxy group (preferably having from 3 to 40 carbon atoms, more preferably from 3 to 30 carbon atoms, and especially preferably from 3 to 24 carbon atoms, e.g., trimethylsilyloxy, triphenylsilyloxy, etc., are exemplified), and a group having a ring structure wherein two substituents are connected to each other to form the ring structure are illustrated. A plural substituents may be the same or different.

As the substituent connected to the nitrogen atom of $Ind^{101}$, an alkyl group, an aryl group, an amino group, an alkoxy group, a halogen atom, a hetero ring group, and a silyl group are preferred, an alkyl group, an aryl group, and a hetero ring group are more preferred. In the case where the substituent is an aryl group or a hetero ring group, the compound having a high charge mobility can be obtained.

Preferred examples of the substituent connected to other part of $Ind^{101}$ than the nitrogen atom include an alkyl group, an aryl group, an amino group, an alkoxy group, a halogen atom, a hetero ring group, and a silyl group. Of these, an alkyl group, an amino group, a halogen atom, a heterocyclic group, and a silyl group are more preferred, with an alkyl group and a halogen atom being particularly preferred. In the case where the substituent is an alkyl group or a halogen atom, the compound having an improved durability can be obtained.

$n^{101}$ represents an integer of 2 or more, preferably 2 to 4, more preferably 2 or 3, particularly preferably 2.

$L^{101}$ represents a $n^{101}$-valent linking group. Examples of the linking group include an aromatic hydrocarbon linking group (containing preferably from 6 to 20 carbon atoms, more preferably from 6 to 10 carbon atoms; specific examples thereof including a benzene ring group, naphthalene ring group, anthracene ring group, pyrene ring group and triphenylene ring group, capable of acting as an $n^{101}$-valent group), a heterocyclic linking group capable of acting as an $n^{101}$-valent group (containing preferably a nitrogen atom, sulfur atom or oxygen atom, more preferably a nitrogen atom, as a hetero atom; containing preferably from 2 to 20 carbon atoms, more preferably from 2 to 5 carbon atoms; the hetero ring being preferably a heteroaromatic ring; specific examples thereof including ring groups such as pyridine, pyrimidine, pyrazine, triazine, thiophene, and oxazine), an alkyl linking group capable of acting as an $n^{101}$-valent group (containing preferably 10 or less carbon atoms, more preferably 6 or less carbon atoms), a silyl linking group capable of acting as an $n^{101}$-valent group, —O—, —N<, and a combination of these linking groups. $L^{101}$ is preferably an alkyl linking group, a silyl linking group, —O—, —N< or a linking group of a combination of these, more preferably an alkyl linking group. When $L^{101}$ represents an alkyl linking group, conjugation within the molecule becomes liable to be interrupted, which serves to maintain the $T_1$ level (the energy level in the state of minimum triplet excitation) at a high level.

The position at which $Ind^{101}$ is connected to $L^{101}$ is 2- or 3-position, preferably 3-position of $Ind^{101}$. When L101 is connected at 2- or 3-position (particularly 3-position) of the indole ring, the durability of the compound can be improved and the device having excellent luminance efficiency and prolonging of life can be obtained.

Formula (2) will be described below.

$R^{201}$ to $R^{206}$ each represents a hydrogen atom or a substituent. The substituent is the same as that above-defined as a substituent in $Ind^{101}$. In the case where $R^{201}$ to $R^{206}$ each represents a substituent, preferred examples of the substituent represented by $R^{201}$ are the same as the preferred examples of substituent connected to the nitrogen atom of $Ind^{101}$, and preferred examples of the substituent represented by $R^{202}$ to $R^{206}$ are the same as the preferred examples of substituent connected to other part of $Ind^{101}$ than the nitrogen atom.

$L^{201}$ represents a linking group. $L^{201}$ is the same as defined for $L^{101}$, and preferred examples thereof are the same as those of $L^{101}$.

$n^{201}$ represents an integer of 2 or more, preferably 2 to 4, more preferably 2 or 3, particularly preferably 2.

Among positions represented by $R^{201}$ to $R^{206}$, preferable positions having a substituent other than a hydrogen atom are as set forth below:

$R^{201}$ is the most preferable position, $R^{204}$ is the second most preferable position, $R^{203}$, $R^{205}$ and $R^{206}$ are the third most preferable positions, and $R^{202}$ is the fourth preferable position.

Formula (3) will be described below.

$R^{301}$ to $R^{306}$ each represents a hydrogen atom or a substituent. The substituent is the same as that above-defined as a substituent in $Ind^{101}$. In the case where $R^{301}$ to $R^{306}$ each represents a substituent, preferred examples of the substituent represented by $R^{301}$ are the same as the preferred examples of substituent connected to the nitrogen atom of $Ind^{101}$, and preferred examples of the substituent represented by $R^{302}$ to $R^{306}$ are the same as the preferred examples of substituent connected to other part of $Ind^{101}$ than the nitrogen atom.

$n^{301}$ represents an integer of 2 or more, preferably 2 or 3, more preferably 2.

$L^{301}$ represents a substituted or unsubstituted atom. When $L^{301}$ represents a substituted or unsubstituted atom, conjugation within the molecule becomes liable to be interrupted, which serves to maintain the $T_1$ level (the energy level in the state of minimum triplet excitation) at a high level. The atom is not particularly limited, and examples thereof include a carbon atom, a silicon atom, a boron atom (in the case where $n^{301} \leq 3$), a nitrogen atom (in the case where $n^{301} \leq 3$), a phosphorus atom (in the case where $n^{301} \leq 3$), an oxygen atom (in the case where $n^{301}=2$), and a sulfur atom (in the case where $n^{301}=2$). The atom is preferably a carbon atom or a silicon atom. The substituents which may be connected to these atoms are the same as those defined as substituents in $Ind^{101}$, and preferred examples of the substituents are an alkyl group, an aryl group, a heterocyclic group, a silyl group, and a halogen atom, more preferred examples thereof are an alkyl group, an aryl group, and a halogen atom, and particularly preferred examples thereof are an alkyl group and an aryl group. The atom is preferably substituted with a substituent. As the substituent, those which have been defined as substituents for $Ind^{101}$, can be applied.

Among positions represented by $R^{301}$ to $R^{306}$, preferable positions having a substituent other than a hydrogen atom are as set forth below:

$R^{301}$ is the most preferable position, $R^{304}$ is the second most preferable position, $R^{303}$, $R^{305}$ and $R^{306}$ are the third most preferable positions, and $R^{302}$ is the fourth preferable position.

Formula (4) will be described below.

$R^{401}$ represents a substituent, and $R^{402}$ to $R^{406}$ each represents a hydrogen atom or a substituent. The substituent is the same as that defined as a substituent which optionally exists in $Ind^{101}$. In the case where $R^{401}$ to $R^{406}$ each represents a substituent, preferred examples of the substituent represented by $R^{401}$ are the same as the preferred examples of substituent connected to the nitrogen atom of $Ind^{101}$, and preferred examples of the substituent represented by $R^{402}$ to $R^{406}$ are the same as the preferred examples of substituent connected to other part of $Ind^{101}$ than the nitrogen atom. $L^{401}$ represents a substituted or unsubstituted atom. The atom is not particularly limited, and examples thereof include a carbon atom, a silicon atom, boron atom (in the case where $n^{401} \leq 3$), a nitrogen atom (in the case where $n^{401} \leq 3$), a phosphorus atom (in the case where $n^{401} \leq 3$), an oxygen atom (in the case where $n^{401} \leq 2$), and a sulfur atom (in the case where $n^{401}=2$). $L^{401}$ is preferably a carbon atom or a silicon atom. The substituents which may be connected to these atoms are the same as those defined as substituents in $Ind^{101}$, and preferred examples of the substituents are an alkyl group, an aryl group, a heterocyclic group, a silyl group, and a halogen atom, more preferred examples thereof are an alkyl group, an aryl group, and a halogen atom, and particularly preferred examples thereof are an alkyl group and an aryl group. $n^{401}$ represents an integer of 2 or more, preferably 2 or 3, more preferably 2. The atom is preferably substituted with a substituent. As the substituent, those which have been defined as substituents for $Ind^{101}$, can be applied.

Among positions represented by $R^{401}$ to $R^{406}$, preferable positions having a substituent other than a hydrogen atom are as set forth below:

$R^{401}$ is the most preferable position, $R^{404}$ is the second most preferable position, $R^{403}$, $R^{405}$ and $R^{406}$ are the third most preferable positions, and $R^{402}$ is the fourth preferable position.

Indole compounds represented by formulae (1) to (3) are preferably incorporated in a hole transporting layer, a hole injecting layer, an exciton blocking layer, a layer adjacent to a light-emitting layer or in a light-emitting layer, more preferably in a hole transporting layer, an exciton blocking layer or a light-emitting layer, particularly preferably in a light-emitting layer.

The specific examples of indole compound according to the invention are shown below, but the invention is not restricted to these compounds.

<Indole Compound>

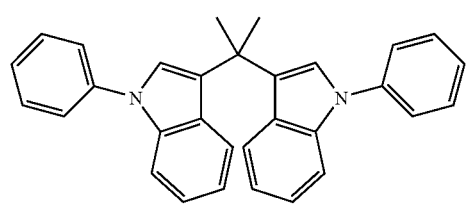

(5-1)

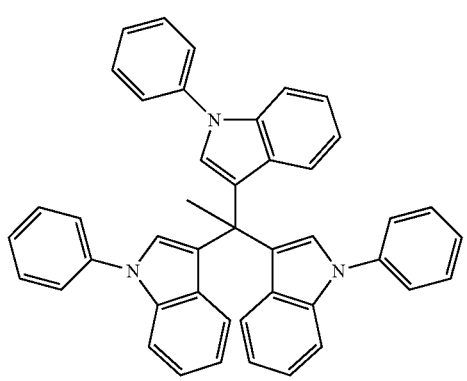

(5-2)

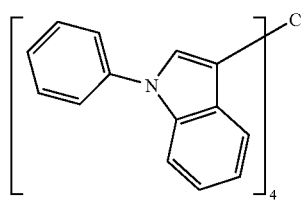
(5-3)
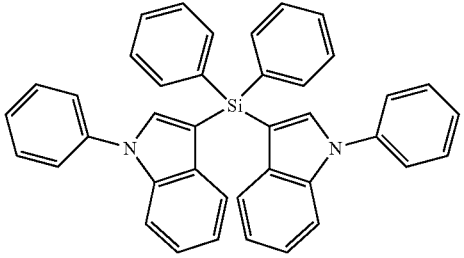
(5-4)
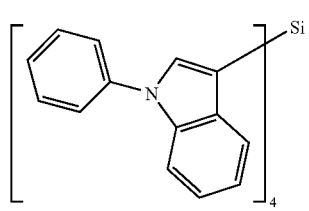
(5-5)
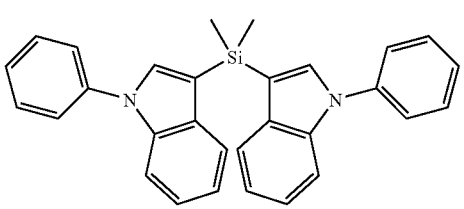
(5-6)
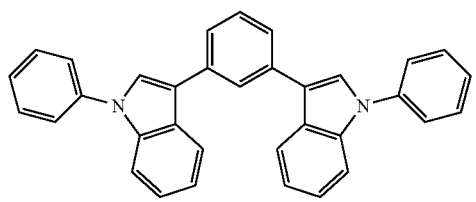
(5-7)
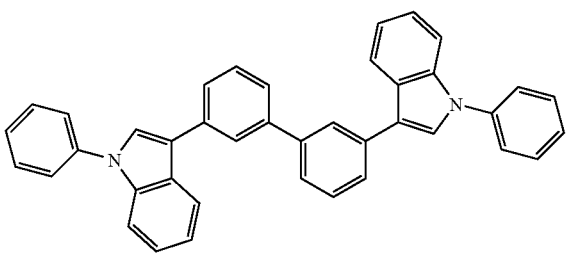
(5-8)
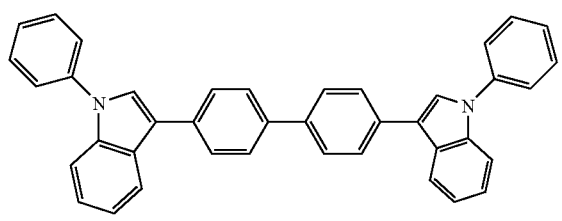
(5-9)
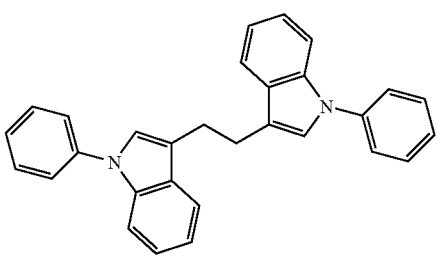
(5-10)
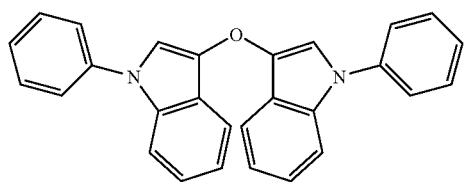
(5-11)
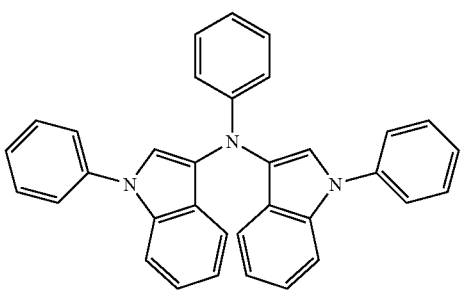
(5-12)

-continued
(5-13)
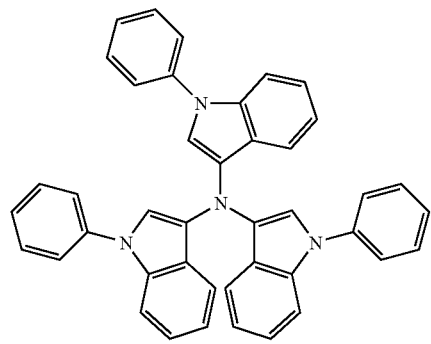
(5-14)
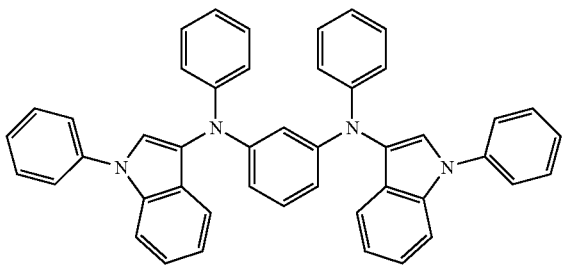
(5-15)
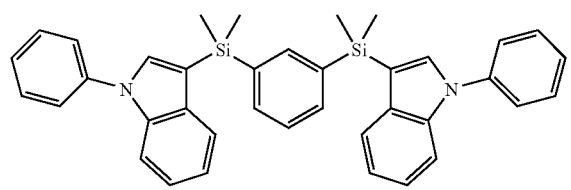
(5-16)
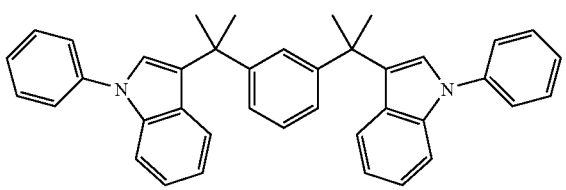
(5-17)
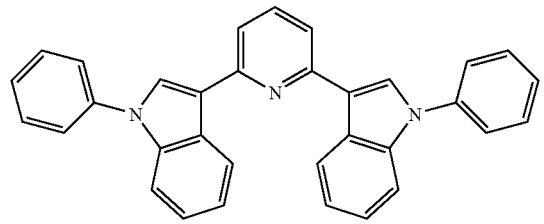
(5-18)
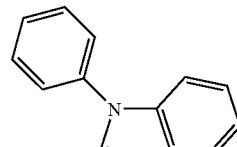
(5-19)
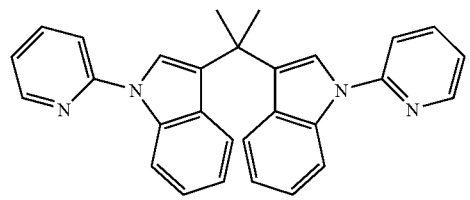
(5-20)
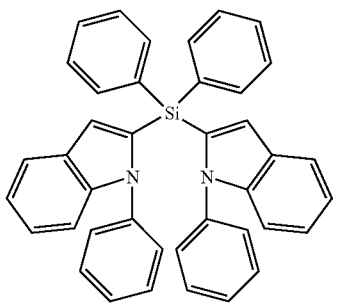
(5-21)
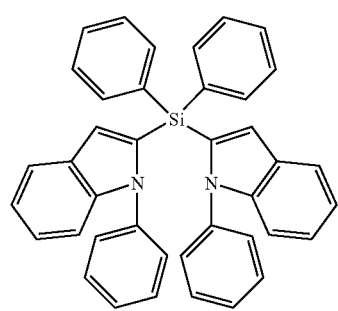
(5-22)

-continued
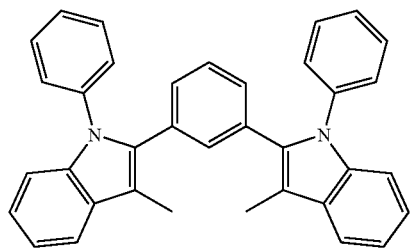
(5-23)
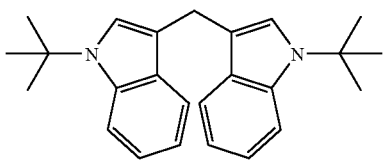
(5-24)
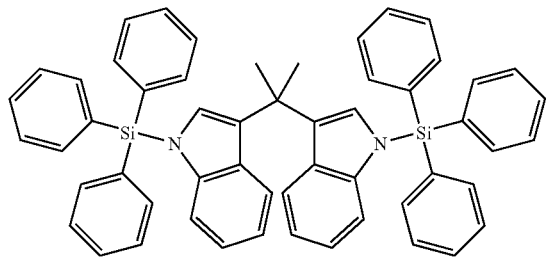
(5-25)
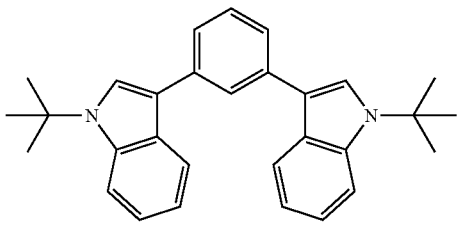
(5-26)
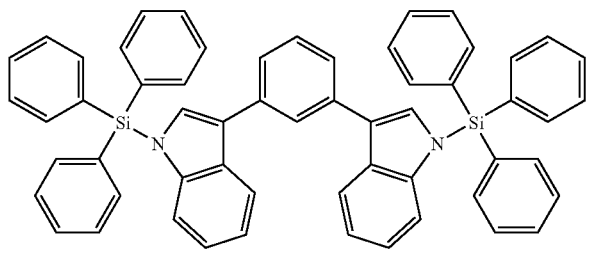
(5-27)
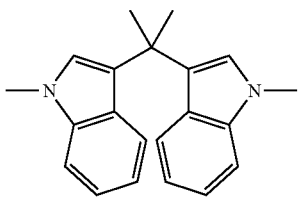
(5-28)
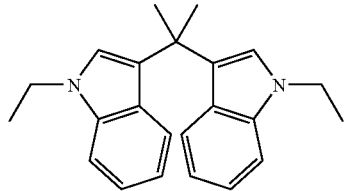
(5-29)
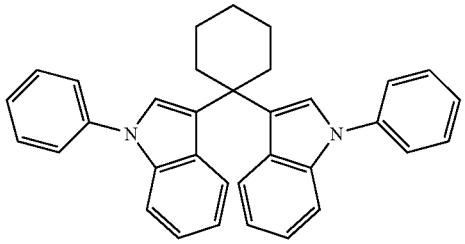
(5-30)
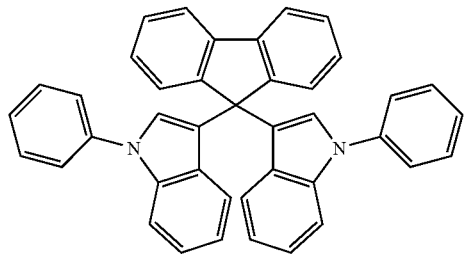
(5-31)
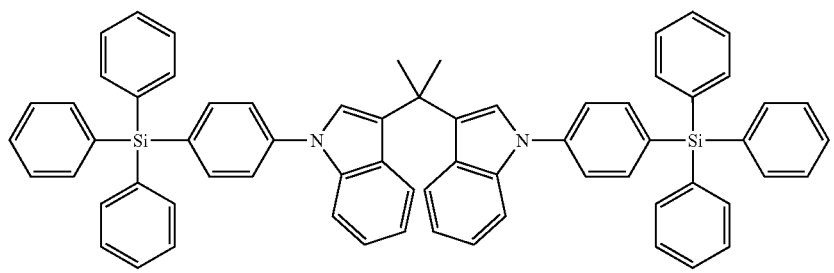
(5-32)

-continued
(5-33) 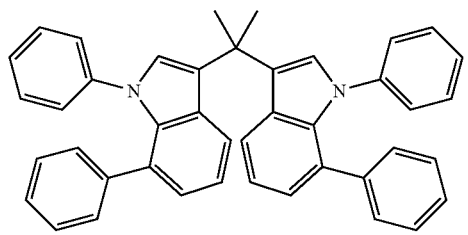
(5-34) 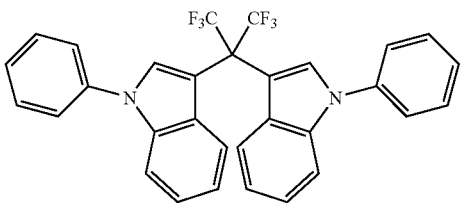
(5-35) 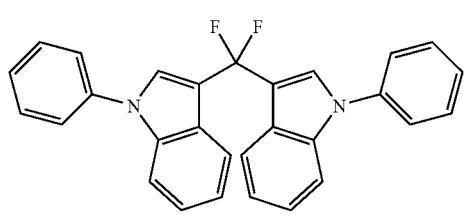
(5-36) 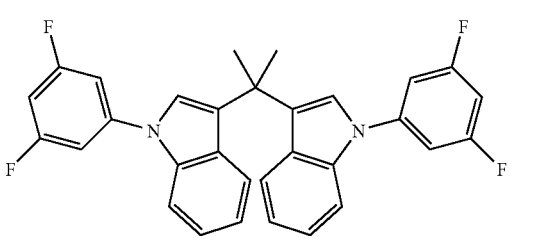
(5-37) 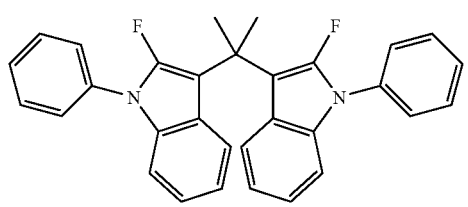
(5-38) 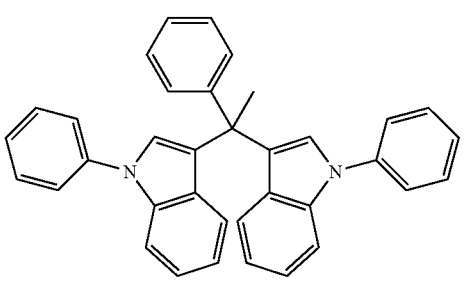
(5-39) 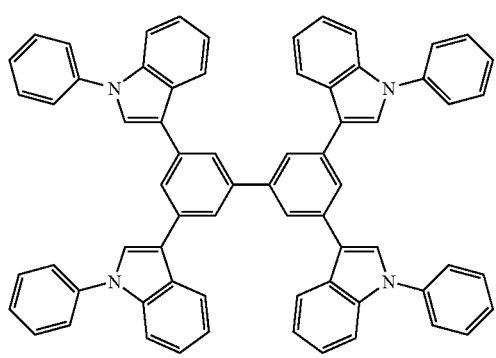
(5-40) 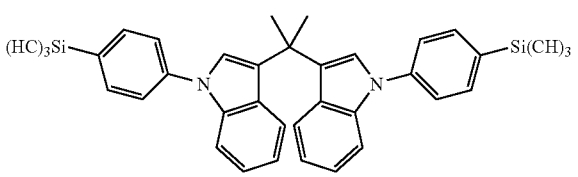
(5-41) 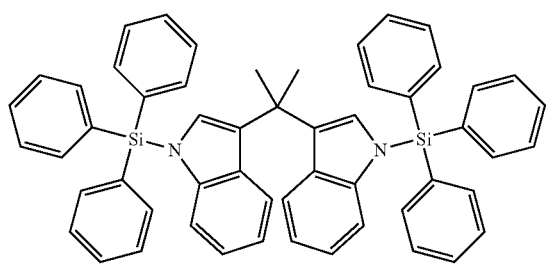
(5-42) 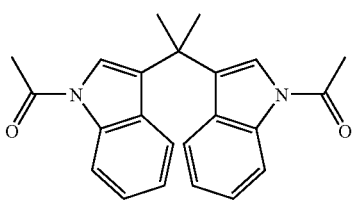

-continued
(5-43)
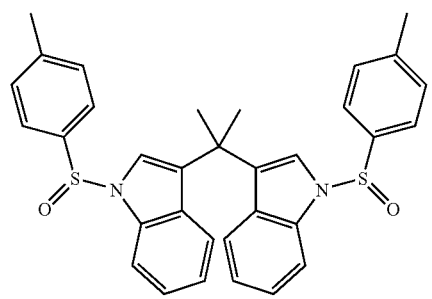
(5-44)
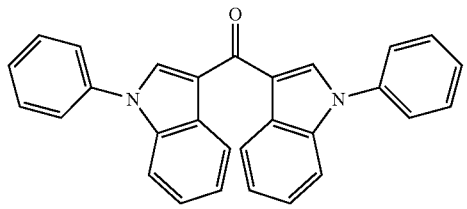
(5-45)
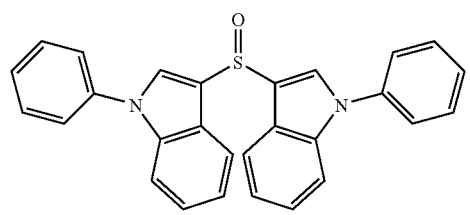
(5-46)
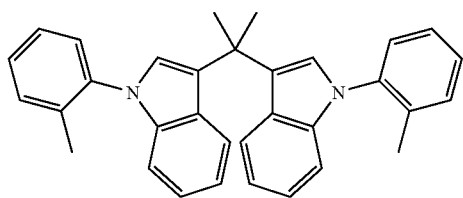
(5-47)
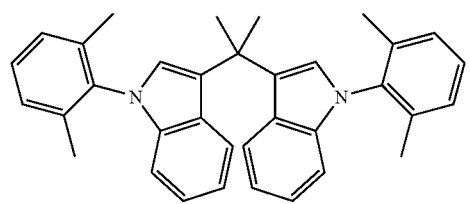
(5-48)
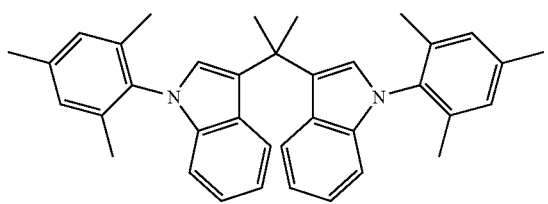
(5-49)
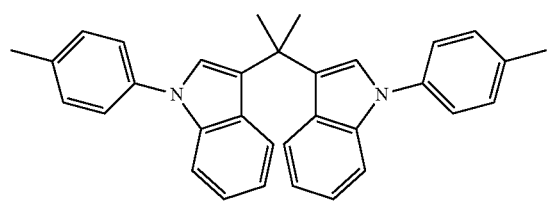
(5-50)
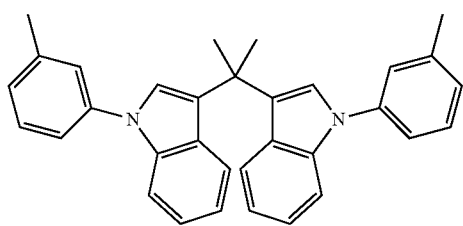
(5-51)
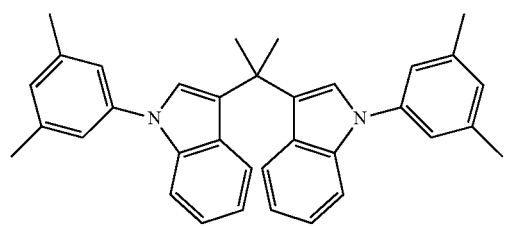
(5-52)
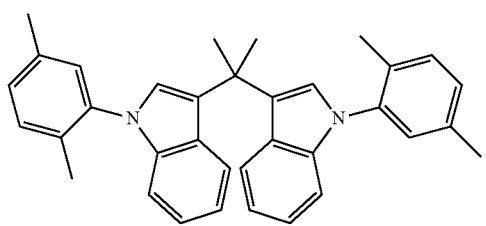
(5-53)
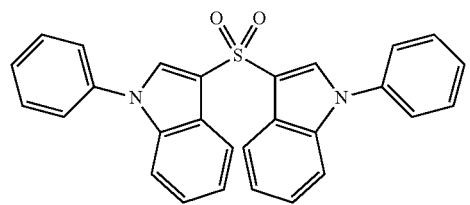
(5-54)
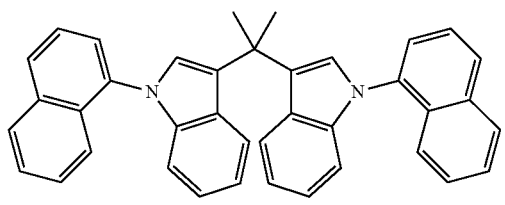

-continued
(5-55)
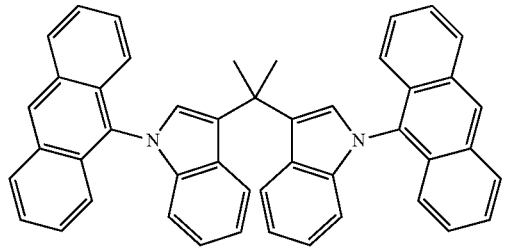
(5-56)
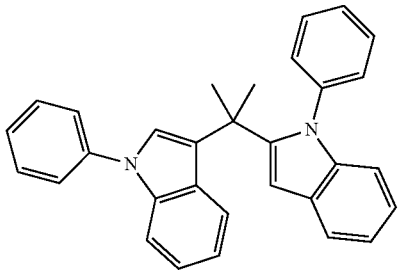
(5-57)
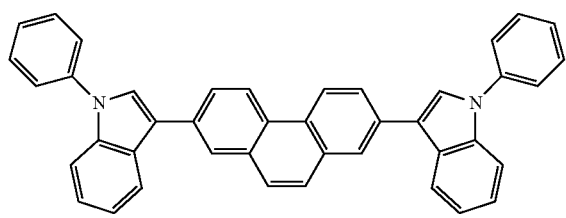
(5-58)
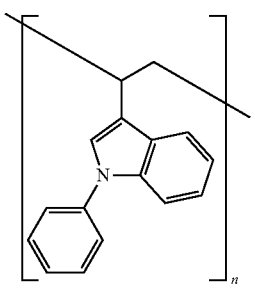
n represents an integer.
(5-59)
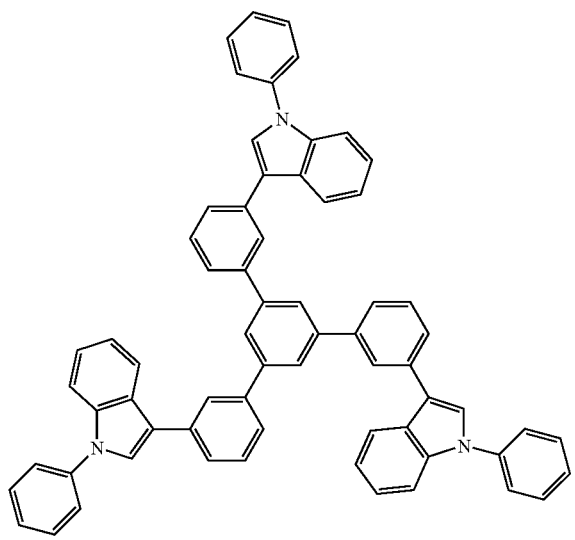
(5-60)
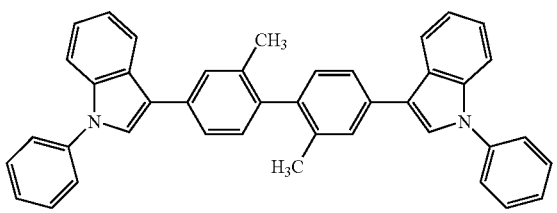
(5-61)
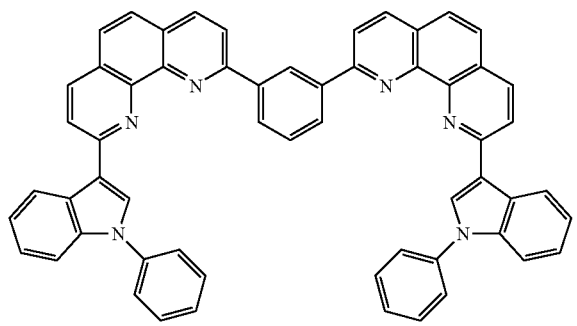
(5-62)
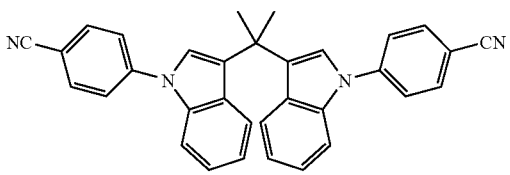

(5-63)
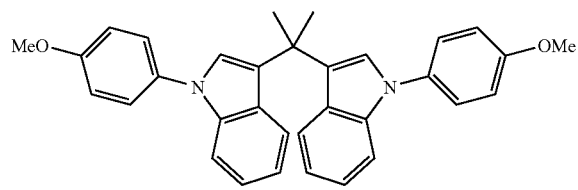
(5-64)
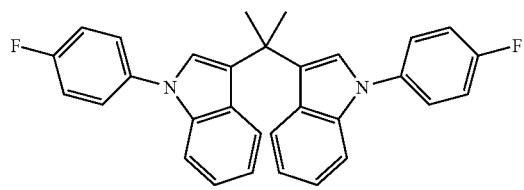
(5-65)
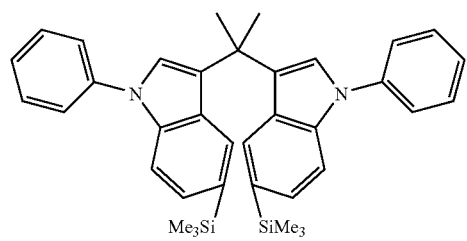
(5-66)
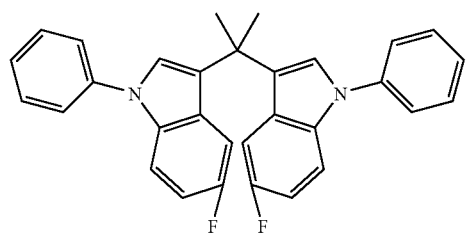
(5-67)
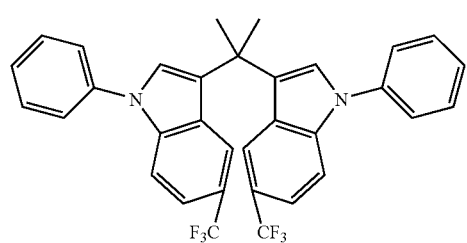
(5-68)
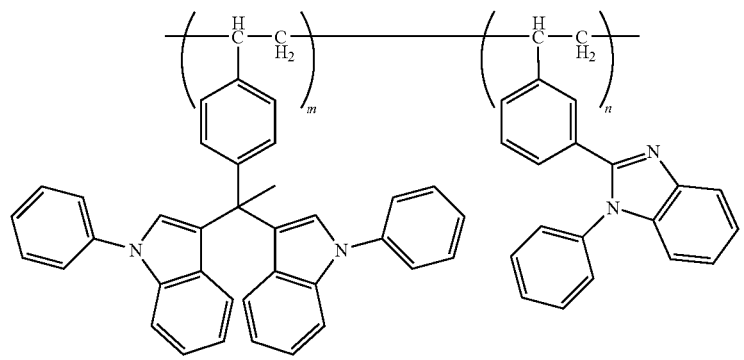
Weight average molecular weight = 15,000
(Weight % ratio: m/n = 70/30)
(5-69)
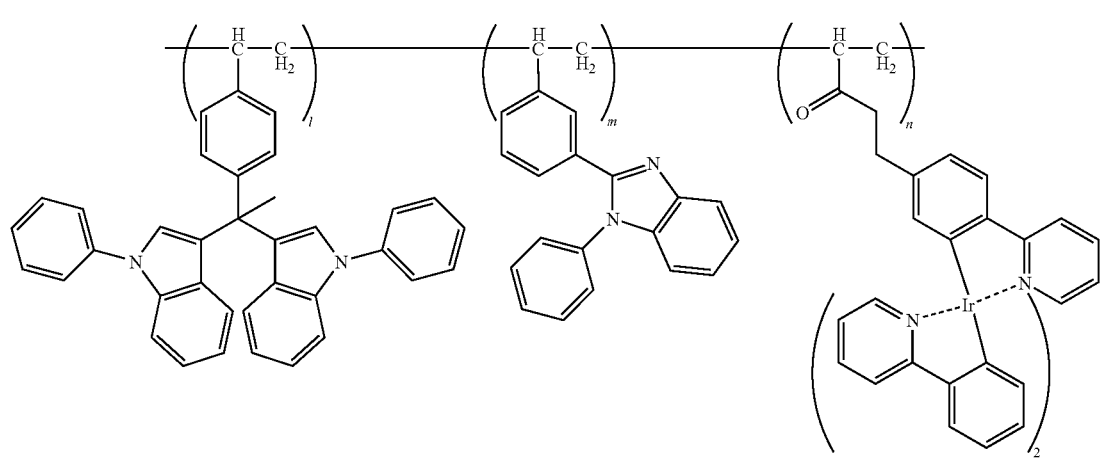
Weight average molecular weight = 13,000
(Weight % ratio: l/m/n = 45/45/10)

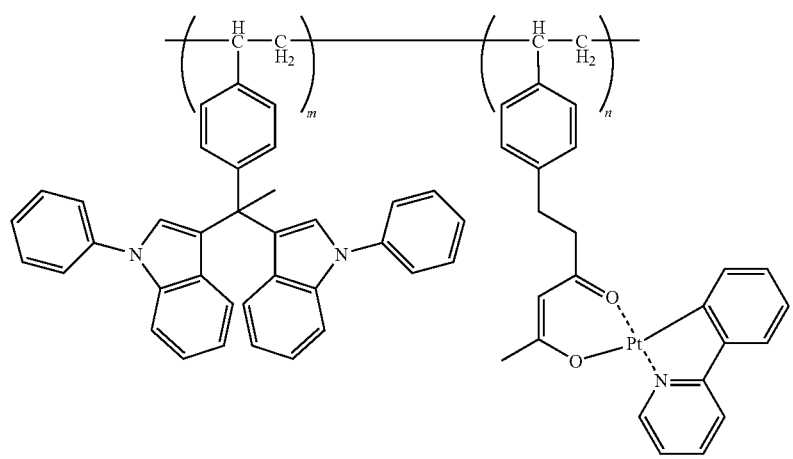

Weight average molecular weight = 20,000
(Weight % ratio: m/n = 95/5)

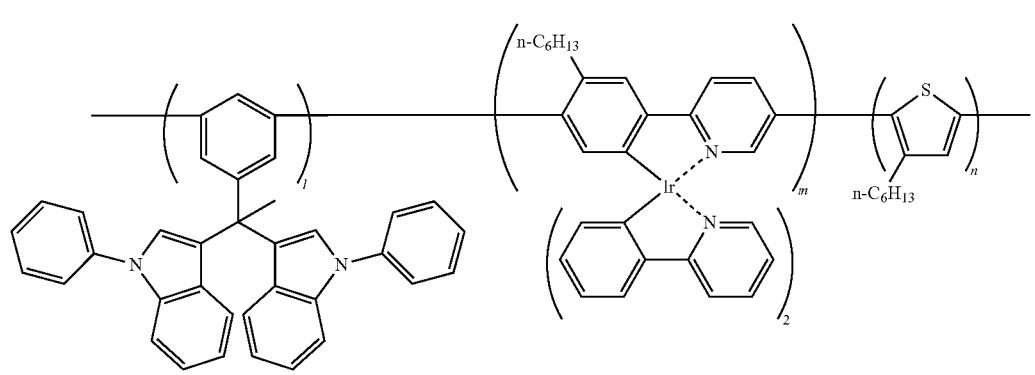

Weight average molecular weight = 11,000
(Weight % ratio: l/m/n = 50/20/30)

Processes for synthesizing indole compounds of the invention will be described below.

Process for synthesizing an indole compound in which indole rings are connected to each other at the 2-position thereof:

A 2-metalloindole is produced by acting a lithium hydrocarbonate, Grignard reagent, or a base on indole or an indole derivative. An indole compound having a substituent at 2-position thereof can be synthesized by acting one of various halides (halosilanes, haloboranes, and halophosphines) on the 2-metalloindole. Also, an end compound can be obtained by trapping the 2-metalloindole with a halogenating agent, and then reacting the product with an amine, alcohol, phenol, alkylboric acid derivative or arylboric acid derivative.

Process for synthesizing an indole compound in which indole rings are connected to each other at the 2-position thereof:

An indole compound wherein indole rings are connected to each other through an alkyl linking can be synthesized by reacting indole or an indole derivative with a ketone or an aldehyde (or an acetal thereof) or an ester (or an orthoester thereof). An indole compound can also be synthesized by halogenating an indole derivative with a halogenating agent to synthesize a 3-haloindole, subjecting this to a halogen-metal exchanging reaction, and reacting the resulting metalloindole with one of various halides (halosilanes, haloboranes, and halophosphines). The 3-haloindole can be reacted with an amine, alcohol, phenol, alkylboric acid derivative or arylboric acid derivative to thereby introduce N, O, alkyl or aryl.

The reaction time for synthesizing an indole compound of the invention varies depending upon the activity of reactants and is not particularly limited, but is preferably from 10 minutes to 24 hours, more preferably from 30 minutes to 15 hours, still more preferably from 1 hour to 10 hours.

The reaction temperature for synthesizing an indole compound of the invention varies depending upon the activity of reactants and is not particularly limited, but is preferably from 100 to 200 ° C., more preferably from 80 to 150 ° C., still more preferably from 60 to 130° C.

An organic electroluminescent device of the invention will be described in detail below.

An organic electroluminescent device in the invention generally includes a substrate having thereon a cathode and an anode, and an organic layer between the electrodes, the organic layer including a light-emitting layer.

An organic electroluminescent device of the invention preferably includes at least three organic layers of a hole transporting layer, a light-emitting layer, and an electron transporting layer. As an embodiment of stacking of the organic layers in the invention, the stacking is preferably in order of a hole transporting layer, a light-emitting layer, and an electron transporting layer from the anode side. Further, a charge blocking layer may be provided between the hole transporting layer and the light-emitting layer, or between the light-emitting layer and the electron transporting layer. A hole injecting layer may be provided between the anode and the hole transporting layer, and an electron injecting layer may be provided between the cathode and the electron transporting layer. Each layer may be divided into a plurality of secondary layers.

Each layer constituting organic layers can be preferably formed by any of dry film-forming methods such as a vacuum deposition method, a sputtering method, etc., a transfer method, and a printing method.

Organic layers in the invention will be described below.
(Light-Emitting layer)

The light-emitting layer is a layer having functions to receive, at the time of applying an electric field, holes from the anode, hole injecting layer or hole transporting layer, and electrons from the cathode, electron injecting layer or electron transporting layer, and to offer the field of recombination of holes and electrons to emit light.

A light-emitting layer in the invention may consist of light-emitting materials alone, or may comprise a mixed layer of a host material and a light-emitting material.

The light-emitting material may be a fluorescent material or may be a phosphorescent material, and more preferably is a phosphorescent material. Dopant may be one or two or more kinds.

The host material is preferably a charge transporting material, and one or two or more host materials may be used. For example, the constitution of the mixture of an electron transporting host material and a hole transporting host material is exemplified. Further, a material not having an electron transporting property and not emitting light may be contained in the light-emitting layer.

A light-emitting layer may include one layer alone or two or more layers, and in the case of two or more layers, each layer may emit light of color different from other layers.
(Fluorescent Material)

The examples of fluorescent materials generally include various metal complexes represented by metal complexes of benzoxazole, benzimidazole, benzothiazole, styrylbenzene, polyphenyl, diphenylbutadiene, tetraphenylbutadiene, naphthalimide, coumarin, pyrane, perinone, oxadiazole, aldazine, pyraridine, cyclopentadiene, bisstyrylanthracene, quinacridone, pyrrolopyridine, thiadiazolopyridine, styrlamine, aromatic dimethylidyne compounds, condensed aromatic compounds (e.g., anthracene, phenanthroline, pyrene, perylene, rubrene, and pentacene), and 8-quinolinol, pyrromethene complexes, and rare earth complexes; polymer compounds such as polythiophene, polyphenylene, polyphenylenevinylene; organic silane; and derivatives thereof.
(Phosphorescent Material)

The examples of phosphorescent materials generally include complexes containing a transition metal atom or a lanthanoid atom.

The transition metal atoms are not especially restricted, but ruthenium, rhodium, palladium, tungsten, rhenium, osmium, iridium, gold, silver, copper, and platinum are preferably exemplified; rhenium, iridium and platinum are more preferred, and iridium and platinum are still more preferred.

As lanthanoid atoms, lanthanum, cerium, praseodymium, neodymium, samarium, europium, gadolinium, terbium, dysprosium, holmium, erbium, thulium, ytterbium, and lutecium are exemplified. Of these lanthanoid atoms, neodymium, europium and gadolinium are preferred.

As the examples of ligands of complexes, the ligands described, for example, in G. Wilkinson et al., Comprehensive Coordination Chemistry, Pergamon Press (1987), H. Yersin, Photochemistry and Photophysics of Coordination Compounds, Springer-Verlag (1987), and Akio Yamamoto, Yuki Kinzoku Kagaku-Kiso to Oyo-(Organic Metal Chemistry—Elements and Applications), Shokabo Publishing Co. (1982) are exemplified.

Specific examples of the ligand include a halogen ligand (preferably, a chlorine ligand), an aromatic hydrocarbon ring ligand (containing preferably from 5 to 30 carbon atoms, more preferably from 6 to 30 carbon atoms, still more preferably from 6 to 20 carbon atoms, particularly preferably from 6 to 12 carbon atoms; e.g., cyclopentadienyl anion, benzene anion, or naphthyl anion), a nitrogen-containing heterocyclic ligand (containing preferably from 5 to 30 carbon atoms, more preferably from 6 to 30 carbon atoms, still more preferably from 6 to 20 carbon atoms, particularly preferably from 6 to 12 carbon atoms; e.g., phenylpyridine, benzoquinoline, quinolinol, bipyridyl or phenanthroline), a diketone ligand (e.g., acetylacetone), a carboxylic acid ligand (containing preferably from 2 to 30 carbon atoms, more preferably from 2 to 20 carbon atoms, still more preferably from 2 to 16 carbon atoms; e.g., acetic acid ligand), an alcoholate ligand (containing preferably from 1 to 30 carbon atoms, more preferably from 1 to 20 carbon atoms, still more preferably from 6 to 20 carbon atoms; e.g., phenolate ligand), a silyloxy ligand (containing preferably from 3 to 40 carbon atoms, more preferably from 3 to 30 carbon atoms, still more preferably from 3 to 20 carbon atoms; e.g., trimethylsilyloxy ligand, dimethyl-tert-buthylsilyloxy ligand, or triphenylsilyloxy ligand), a carbon monoxide ligand, an isonitrile ligand, a cyano ligand, a phosphorus ligand (containing preferably from 3 to 40 carbon atoms, more preferably from 3 to 30 carbon atoms, still more preferably from 3 to 20 carbon atoms, particularly preferably from 6 to 20 carbon atoms; e.g., triphenylphosphine ligand), a thiolate ligand (containing preferably from 1 to 30 carbon atoms, more preferably from 1 to 20 carbon atoms, still more preferably from 6 to 20 carbon atoms; e.g., phenylthiolate ligand), and a phosphine oxide ligand (containing preferably from 3 to 30 carbon atoms, more preferably from 8 to 30 carbon atoms, still more preferably from 18 to 30 carbon atoms; e.g., triphenylphosphine oxide ligand). The nitrogen-containing heterocyclic ligands are more preferred.

The complex may have one transition metal atom in the compound, or may be a so-called multi-nuclear complex having two or more transition metal atoms, or may simultaneously contain different kinds of metal atoms.

Of these, phosphorescent compounds described in patents, for example, U.S. Pat. No. 6,303,238 B1, U.S. Pat. No. 6,097,147, WO 00/57676, WO 00/70655, WO 01/08230, WO 01/39234 A2, WO 01/41512 A1, WO 02/02714 A2, WO 02/15645 A1, WO 02/44189 A1, WO 05/19373 A2, JP-A-2001-247859, JP-A-2002-302671, JP-A-2002-117978, JP-A-2003-133074, JP-A-2002-235076, JP-A-2003-123982, JP-A-2002-170684, EP1211257, JP-A-2002-226495, JP-A-2002-234894, JP-A-2001-247859, JP-A-2001-298470, JP-A-2002-173674, JP-A-2002-203678, JP-A-2002-203679, JP-A-2004-357791, JP-A-2006-256999, JP-A-2007-19462, JP-A-2007-84635, and JP-A-2007-96259 are illustrated as specific examples of the light-emitting material. Examples of still more preferred light-emitting materials include complexes of Ir, Pt, Cu, Re, W, Rh, Ru, Pd, Os, Eu, Tb, Gd, Dy, and Ce. Ir, Pt and Re complexes are particularly preferred, and Ir, Pt and Re complexes having at least one coordination mode such as metal-carbon bond, metal-nitrogen bond, metal-oxygen bond, and metal sulfur bond are preferred among them. Further, in view of luminance efficiency, driving durability, and chromaticity, Ir complexes, Pt complexes, and Re complexes containing polydentate ligands having three or more coordination sites are particularly preferred, with Ir complexes and Pt complexes being most preferred. Of them, Pt complexes having a tetradentate ligand (quadridentate ligand) are particularly preferred.

Light-emitting materials are not particularly limited, but use of a phosphorescent material is preferred. Use of a phosphorescent material of an iridium complex or a platinum complex is more preferred, and use of a phosphorescent material having a tetradentate ligand is particularly preferred. However, other phosphorescent materials may be used together with them.

As the complex phosphorescent materials, there can be illustrated compounds described in Coordination Chemistry Reviews 250 (2006), 2093-2126.

As the iridium complex phosphorescent materials, there can be illustrated compounds described in WO 00/70655, WO 01/41512, WO 02/5645, JP-A-2002-117978, WO 04/085450, WO 06/121811, WO 05/019373, and WO 05/113704.

The specific examples of the platinum complex phosphorescent material having a tetradentate ligand include compounds disclosed in WO 2004/108857.

As the platinum complex phosphorescent material having a tetradentate ligand, more specifically, preferred are compounds described in U.S. Pat. No. 6,653,654, WO 2004/099339, WO 2004/108857, JP-A-2005-310733, JP-A-2005-317516, JP-A-2006-261623, JP-A-2006-93542, JP-A-2006-256999, WO 2006/098505, JP-A-2007-19462, JP-A-2007-96255, JPA-2007-96259, WO 2005/042444, JP-A-2006-232784, US 2006/0134461, and WO 2005/042550.

As the platinum complex (phosphorescent) material having a tetradentate ligand, those containing a 2-arylpyridine derivative, a 2-(1-pyrazolyl)pyridine derivative or a 1-arylpyrazole derivative as a partial structure of the ligand are preferred; those containing a 2-arylpyridine derivative or a 2-(1-pyrazolyl)pyridine derivative as a partial structure of the ligand are more preferred, and those containing a 1-arylpyrazole derivative as a partial structure of the ligand are particularly preferred.

The above-described partial structures of the ligand (e.g., a 2-arylpyridine derivative, a 2-(1-pyrazolyl)pyridine derivative, and a 1-arylpyrazole derivative) are connected to each other at an appropriate site thereof to constitute a tetradentate ligand.

In the case where the ligand contains 2-arylpyridine derivatives as a partial structure thereof, the 2-arylpyridine derivatives are connected to each other preferably in such manner that one 2-arylpyridine derivative is connected, at 6-position of the pyridine ring and/or m-position of the aryl group with respect to the pyridine ring thereof, to the other 2-arylpyridine derivative at 6-position of the pyridine ring and/or m-position of the aryl group with respect to the pyridine ring thereof; more preferably in such manner that the two 2-arylpyridine derivatives are connected to each other each at 6-position of the pyridine ring thereof or each at m-position of the aryl group with respect to the pyridine ring thereof; and particularly preferably in such manner that the two 2-arylpyridine derivatives are connected to each other each at 6-position of the pyridine ring thereof.

In the case where the ligand contains 2-(1-pyrazolyl)pyridine derivatives as a partial structure thereof, the 2-(1-pyrazolyl)pyridine derivatives are connected to each other preferably in such manner that one 2-(1-pyrazolyl)pyridine derivative is connected, at 6-position of the pyridine ring and/or 4-position of the 1-pyrazolyl group thereof, to the other 2-(1-pyrazolyl)pyridine derivative at 6-position of the pyridine ring and/or 4-position of the 1-pyrazolyl group thereof; more preferably in such manner that the two 2-(1-pyrazolyl)pyridine derivatives are connected to each other each at 6-position of the pyridine ring thereof or each at 4-position of the 1-pyrazolyl group thereof; and particularly preferably in such manner that the two 2-(1-pyrazolyl)pyridine derivatives are connected to each other each at 6-position of the pyridine ring thereof.

In the case where the ligand contains 1-arylpyrazole derivatives as a partial structure thereof, the 1-arylpyrazole derivatives are connected to each other preferably in such manner that one 1-arylpyrazole derivative is connected, at 3-position of the pyrazole ring and/or m-position of the aryl group with respect to the pyrazole ring thereof, to the other 1-arylpyrazole derivative at 3-position of the pyrazole ring and/or m-position of the aryl group with respect to the pyrazole ring thereof; more preferably in such manner that the two 1-arylpyrazole derivatives are connected to each other each at 3-position of the pyrazole ring thereof or each at m-position of the aryl group with respect to the pyrazole ring thereof; and particularly preferably in such manner that the two 1-arylpyrazole derivatives are connected to each other each at 3-position of the pyrazole ring thereof.

The structure linking the partial structures of the ligand may be a single bond or a divalent linking bond, with a divalent linking bond being preferred. The divalent linking group is preferably a linking group of methylene, a linking group of ethylene, a linking group of phenylene, a linking group of nitrogen atom, a linking group of oxygen atom, a linking group of sulfur atom, or a linking group of silicon atom, more preferably a linking group of methylene, a linking group of nitrogen atom, or a linking group of silicon atom, particularly preferably a linking group of methylene. Specific examples of the linking group of methylene include a methylene group (—CH$_2$—), a methylmethylene group (—CHMe-), a fluoromethylmethylene group (—CFMe-), a dimethylmethylene group (—CMe$_2$-), a methylphenylmethylene group (—CMePh—), a diphenylmethylene group (—CPh$_2$—), a 9,9-fluorendiyl group, a 1,1-cyclopentandiyl group, and a 1,1-cyclohexandiyl group. Of these, a dimethylmethylene group, a diphenylmethylene group, a 9,9-fluorendiyl group, a 1,1-cyclopentandiyl group, and a 1,1-cyclohexandiyl group are preferred, a dimethylmethylene group, a diphenylmethylene group, and a 1,1-cyclohexandiyl group are more preferred, and a dimethylmethylene group is particularly preferred.

Also, one of more preferred examples of the platinum complex phosphorescent material having a tetradentate ligand is a Pt complexe represented by the following formula (A).

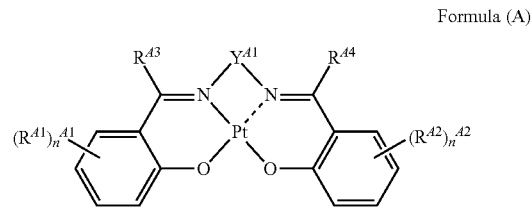

Formula (A)

In the formula (A), $R^{43}$ and $R^{44}$ each independently represents a hydrogen atom or a substituent, and $R^{41}$ and $R^{42}$ each independently represents a substituent. In the case where plural $R^{41}$s and $R^{42}$s exist, they may be the same or different, or may be connected to each other to form a ring. $n^{41}$ and $n^{42}$ each independently represents an integer of from 0 to 4. $Y^{41}$ represents a linking group.

As substituents represented by $R^{41}$, $R^{42}$, $R^{43}$, and $R^{44}$, any one can be selected from the following substituent group A.

Substituent group A:

An alkyl group (containing preferably from 1 to 30 carbon atoms, more preferably from 1 to 20 carbon atoms, particularly preferably from 1 to 10 carbon atoms; for example, a methyl group, an ethyl group, an iso-propyl group, a tert-butyl group, a n-octyl group, a n-decyl group, a n-hexadecyl group, a cyclopropyl group, a cyclopentyl group or a cyclohexyl group), an alkenyl group (containing preferably from 2 to 30 carbon atoms, more preferably from 2 to 20 carbon atoms, particularly preferably from 2 to 10 carbon atoms; for example, a vinyl group, an allyl group, a 2-butenyl group or a 3-pentenyl group); an alkynyl group (containing preferably from 2 to 30 carbon atoms, more preferably from 2 to 20 carbon atoms, particularly preferably from 2 to 10 carbon atoms; for example, a propargyl group or a 3-pentynyl group); an aryl group (containing preferably from 6 to 30 carbon atoms, more preferably from 6 to 20 carbon atoms, particularly preferably from 6 to 12 carbon atoms; for example, a phenyl group, a p-methylphenyl group, a naphthyl group or an anthranyl group), an amino group (containing preferably from 0 to 30 carbon atoms, more preferably from 0 to 20 carbon atoms, particularly preferably from 0 to 10 carbon atoms; for example, an amino group, a methylamino group, a dimethylamino group, a diethylamino group, a dibenzylamino group, a diphenylamino group or a ditolylamino group), an alkoxy group (containing preferably from 1 to 30 carbon atoms, more preferably from 1 to 20 carbon atoms, particularly preferably from 1 to 10 carbon atoms; for example, a methoxy group, an ethoxy group, a butoxy group or a 2-ethylhexyloxy group), an aryloxy group (containing preferably from 6 to 30 carbon atoms, more preferably from 6 to 20 carbon atoms, particularly preferably from 6 to 12 carbon atoms; for example, a phenyloxy group, a 1-naphthyloxy group or a 2-naphthyloxy group), a heterocyclic oxy group (containing preferably from 1 to 30 carbon atoms, more preferably from 1 to 20 carbon atoms, particularly preferably from 1 to 12 carbon atoms; for example, a pyridyloxy group, a pyrazyloxy group, a pyrimidyloxy group or a quinolyloxy group), an acyl group (containing preferably from 1 to 30 carbon atoms, more preferably from 1 to 20 carbon atoms, particularly preferably from 1 to 12 carbon atoms; for example, an acetyl group, a benzoyl group, a formyl group or a pivaloyl group), an alkoxycarbonyl group (containing preferably from 2 to 30 carbon atoms, more preferably from 2 to 20 carbon atoms, particularly preferably from 2 to 12 carbon atoms; for example, a methoxycarbonyl group or an ethoxycarbonyl group), an aryloxycarbonyl group (containing preferably from 7 to 30 carbon atoms, more preferably from 7 to 20 carbon atoms, particularly preferably from 7 to 12 carbon atoms; for example, a phenyloxycarbonyl), an acyloxy group (containing preferably from 2 to 30 carbon atoms, more preferably from 2 to 20 carbon atoms, particularly preferably from 2 to 10 carbon atoms; for example, an acetoxy group or a benzoyloxy group), an acylamino group (containing preferably from 2 to 30 carbon atoms, more preferably from 2 to 20 carbon atoms, particularly preferably from 2 to 10 carbon atoms; for example, an acetylamino group or a benzoylamino group), an alkoxycarbonylamino group (containing preferably from 2 to 30 carbon atoms, more preferably from 2 to 20 carbon atoms, particularly preferably from 2 to 12 carbon atoms; for example, a methoxycarbonylamino group), an aryloxycarbonylamino group (containing preferably from 7 to 30 carbon atoms, more preferably from 7 to 20 carbon atoms, particularly preferably from 7 to 12 carbon atoms; for example, a phenyloxycarbonylamino group), a sulfonylamino group (containing preferably from 1 to 30 carbon atoms, more preferably from 1 to 20 carbon atoms, particularly preferably from 1 to 12 carbon atoms; for example, a methanesulfonylamino group or a benzenesulfonylamino group), a sulfamoyl group (containing preferably from 0 to 30 carbon atoms, more preferably from 0 to 20 carbon atoms, particularly preferably from 0 to 12 carbon atoms; for example, a sulfamoyl group, a methylsulfamoyl group, a dimethylsulfamoyl group or a phenylsulfamoyl group), a carbamoyl group (containing preferably from 1 to 30 carbon atoms, more preferably from 1 to 20 carbon atoms, particularly preferably from 1 to 12 carbon atoms; for example, a carbamoyl group, a methylcarbamoyl group, a diethylcarbamoyl group or a phenylcarbamoyl group), an alkylthio group (containing preferably from 1 to 30 carbon atoms, more preferably from 1 to 20 carbon atoms, particularly preferably from 1 to 12 carbon atoms; for example, a methylthio group or an ethylthio group), an arylthio group (containing preferably from 6 to 30 carbon atoms, more preferably from 6 to 20 carbon atoms, particularly preferably from 6 to 12 carbon atoms; for example, a phenylthio group), a heterocyclic thio group (containing preferably from 1 to 30 carbon atoms, more preferably from 1 to 20 carbon atoms, particularly preferably from 1 to 12 carbon atoms; for example, a pyridylthio group, a 2-benzimidazolylthio group, a 2-benzoxazolylthio group or a 2-benzothiazolylthio group), a sulfonyl group (containing preferably from 1 to 30 carbon atoms, more preferably from 1 to 20 carbon atoms, particularly preferably from 1 to 12 carbon atoms; for example, a mesyl group or a tosyl group), a sulfinyl group (containing preferably from 1 to 30 carbon atoms, more preferably from 1 to 20 carbon atoms, particularly preferably from 1 to 12 carbon atoms; for example, a methanesulfinyl group or a benzenesulfinyl group), a ureido group (containing preferably from 1 to 30 carbon atoms, more preferably from 1 to 20 carbon atoms, particularly preferably from 1 to 12 carbon atoms; for example, a ureido group, a methylureido group or a phenylureido group), a phosphoric acid amide group (containing preferably from 1 to 30 carbon atoms, more preferably from 1 to 20 carbon atoms, particularly preferably from 1 to 12 carbon atoms; for example, a diethylphosphoric acid amide group or a phenylphosphoric acid amide group), a hydroxyl group, a mercapto group, a halogen atom (for example, a fluorine atom, a chlorine atom, a bromine atom or an iodine atom), a cyano group, a sulfo group, a carboxyl group, a nitro group, a hydroxamic acid group, a sulfino group, a hydrazino group, an imino group, a heterocyclic group (containing preferably from 1 to 30 carbon atoms, more preferably from 1 to 12 carbon atoms; hetero atom being, for example, nitrogen atom, oxygen atom or sulfur atom; specific examples including an imidazolyl group, a pyridyl group, a quinolyl group, a furyl group, a thienyl group, a piperidyl group, a morpholino group, a benzoxazolyl group, a benzimidazolyl group, a benzothiazolyl group, a carbazolyl group or an azepinyl group), a silyl group (containing preferably from 3 to 40 carbon atoms, more preferably from 3 to 30 carbon atoms, particularly preferably from 3 to 24 carbon atoms; for example, a trimethylsilyl group or a triphenylsilyl group), a silyloxy group (containing preferably from 3 to 40 carbon atoms, more preferably from 3 to 30 carbon atoms, particularly preferably from 3 to 24 carbon atoms; for example, a trimethylsilyloxy group or a triphenylsilyloxy group), and a phosphoryl group (for example, a diphenylphosphoryl group or a dimethylphosphoryl group).

As the linking group represented by $Y^{41}$, any one can be selected from the following group A of the linking group.

Group A of the Linking Group:

An alkylene group (for example, methylene, ethylene or propylene), an arylene group (for example, phenylene or naphthalenediyl), a hetero arylene group (for example, pyridinediyl or thiophenediyl), an imino group (—NR—) (for example, a phenylimino group), an oxy group (—O—), a thio group (—S—), a phosphinidene group (—PR—) (for example, a phenylphosphinidene group), a silylene group (—SiRR'—) (for example, a dimethylsilylene group or a diphenylsilylene group), and a combination thereof. These linking groups may further have a substituent.

As substituents represented by $R^{41}$, $R^{42}$, $RA^3$, and $R^{44}$, an alkyl group, an aryl group, and a heterocyclic group are preferred, an aryl group and a heterocyclic group are more preferred, and an aryl group is particularly preferred.

As the linking group represented by $Y^{41}$, a vinyl group, phenylene ring, a pyridine ring, pyrazine ring, or pyrimidine ring which are connected to the nitrogen atoms at 1- and 2-positions thereof, or an alkylene group containing from 1 to 8 carbon atoms is preferred, a vinyl group or phenylene ring which are connected to the nitrogen atoms at 1 and 2-positions thereof, or an alkylene group containing from 1 to 6 carbon atoms is more preferred, and a phenylene ring is particularly preferred.

The substituents represented by $R^{43}$ and $R^{44}$ may be connected to the linking group represented by $Y^{41}$ to form a ring. For example, in the case where $Y^{41}$ represents a phenylene group connected to the nitrogen atoms at 1- and 2-positions thereof, $R^{43}$ and $R^{44}$ may respectively be connected to 3- and 6-positions of the phenylene group to form a phenanthroline ring and may further have a substituent.

One f more preferred examples of the platinum complex phosphorescent material having a tetradentate ligand is a Pt complexe represented by the following formula (B).

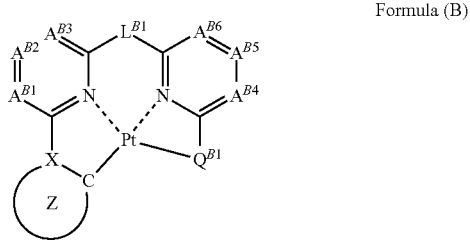

Formula (B)

In the formula (B), $A^{B1}$ to $A^{B6}$ each independently represents C—R or N. R represents a hydrogen atom or a substituent. $L^{B1}$ represents a divalent linking group. X represents C or N. Z represents a 5- or 6-membered aromatic or heteroaromatic ring formed together with X—C. $Q^{B1}$ represents an anionic group connected to Pt.

The formula (B) will be described below.

$A^{B1}$ to $A^{B6}$ each independently represents C—R or N. R represents a hydrogen atom or a substituent. The Substituent represented by R is the same as those which have been illustrated as the foregoing substituent group A, and a preferred scope thereof is also the same as described there.

$A^{B1}$ to $A^{B6}$ each is preferably C—R, and Rs may be connected to each other to form a ring. In the case where $A^{B1}$ to $A^{B6}$ each represents C—R, R in each of $A^{B2}$ and $A^{B5}$ is preferably a hydrogen atom, an alkyl group, an aryl group, an amino group, an alkoxy group, an aryloxy group, a fluorine atom or a cyano group; more preferably a hydrogen atom, an amino group, an alkoxy group, an aryloxy group or a fluorine atom; and particularly preferably a hydrogen atom or a fluorine atom, and R in each of $A^{B1}$, $A^{B3}$, $A^{B4}$, and $A^{B6}$ is preferably a hydrogen atom, an alkyl group, an aryl group, an amino group, an alkoxy group, an aryloxy group, a fluorine atom or a cyano group; more preferably a hydrogen atom, an amino group, an alkoxy group, an aryloxy group or a fluorine atom; and particularly preferably a hydrogen atom.

$L^{B1}$ represents a single bond or a divalent linking group.

Examples of the divalent linking group represented by $L^{B1}$ include an alkylene group (e.g., methylene, ethylene or propylene), an arylene group (e.g., phenylene or naphthalenediyl), a heteroarylene group (e.g., pyridinediyl or thiophenediyl), an imino group (—NR—) (e.g., a phenylimino group), an oxy group (—O—), a thio group (—S—), a phosphinidene group (—PR—) (e.g., a phenylphosphinidene group), a silylene group (—SiRR'—) (e.g., a dimethylsilylene group or a diphenylsilylene group), and a combination thereof These linking groups may further have a substituent.

$L^{B1}$ represents preferably a single bond, an alkylene group, an arylene group, a heteroarylene group, an imino group, an oxy group, a thio group or a silylene group; more preferably a single bond, an alkylene group, an arylene group or an imino group; still more preferably an alkylene group; still more preferably a methylene group; still more preferably a di-substituted methylene group; still more preferably a dimethylmethylene group, a diethylmethylene group, a diisobutylmethylene group, a dibenzylmethylene group, an ethylmethylmethylene group, a methylpropylmethylene group, an isobutylmethylmethylene group, a diphenylmethylene group, a methylphenylmethylene group, a cyclohexanediyl group, a cyclopentanediyl group, a fluorenediyl group or a fluoromethylmethylene group; and particularly preferably a dimethylmethylene group, a diphenylmethylene group or a cyclohexanediyl group.

X represents C or N. Z represents a 5- or 6-membered aromatic hydrocarbon romg or heteroaromatic ring formed together with X—C. Examples of the aromatic hydrocarbon ring or heteroaromatic ring represented by Z include a benzene ring, a naphthalene ring, an anthracene ring, a pyrene ring, a phenanthrene ring, a perylene ring, a pyridine ring, a quinoline ring, an isoquinoline ring, a phenanthridine ring, a pyrimidien ring, a pyrazine ring, a pyridazine ring, a triazine ring, cinnoline ring, an acridine ring, a phthalazine ring, a quinazoline ring, a quinoxaline ring, a naphthyridine ring, a pteridine ring, a pyrrole ring, a pyrazole ring, a triazole ring, an indole ring, a carbazole ring, an indazole ring, a benzimidazole ring, an oxazole ring, a thiazole ring, an oxadiazole ring, a thiadiazole ring, a benzoxazole ring, a benzothiazole ring, an imidazopyridine ring, a thiophene ring, a benzothiophene ring, a furan ring, a benzofuran ring, a phosphole ring, a phosphinine ring, and a silole ring. Z may contain a substituent. As the substituent, those which have heretofore been illustrated as the substituent group A may be applied. In addition, Z may form a condensed ring together with other ring.

Z is preferably a benzene ring, a naphthalene ring, a pyrazole ring, an imidazole ring, a triazole ring, a pyridine ring, an indole ring or a thiophene ring, more preferably a benzene ring, a pyrazole ring or a pyridine ring.

$Q^{B1}$ represents an anionic group connected to Pt. Examples of the anionic group represented by $Q^{B1}$ include a vinyl ligand, an aromatic hydrocarbon ring ligand (e.g., a benzene ligand, a naphthalene ligand, an anthracene ligand or a phenanthrene ligand), a heterocyclic ligand (e.g., a furan ligand, a thiophene ligand, a pyridine ligand, a pyrazine ligand, a pyrimidine ligand, a pyridazine ligand, a triazine ligand, a thiazole ligand, an oxazole ligand, a pyrrole ligand, an imidazole ligand, a pyrazole ligand, a triazole ligand, and a ring-condensed ligand thereof (e.g., a quinoline ligand or a benzothiazole ligand). In this case, the bond between Pt and $Q^{B1}$ may be any of covalent bond, ionic bond and coordination bond. As the atom in $Q^{B1}$ connected to Pt, a carbon atom, a nitrogen atom, an oxygen atom, a sulfur atom, and a phosphorus atom are preferred, a carbon atom, an oxygen atom, and a nitrogen atom are more preferred, and a carbon atom is still more preferred.

The group represented by $Q^{B1}$ is preferably an aromatic hydrocarbon ring ligand connected to Pt at the carbon atom thereof, an aromatic heterocyclic ligand connected to Pt at the carbon atom thereof, a nitrogen-containing aromatic heterocyclic ligand connected to Pt at the nitrogen atom thereof, or an acyloxy ligand, more preferably an aromatic hydrocarbon ring ligand connected to Pt at the carbon atom thereof, or an aromatic heterocyclic ligand connected to Pt at the carbon atom thereof It is particularly preferred that the group represented by $Q^{B1}$ is the same group as Z ring formed together with C—X in the formula (B).

The Pt complex represented by the formula (B) is more preferably a Pt complex represented by the following formula (C).

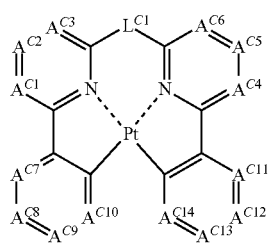

Formula (C)

In the formula (C), $A^{C1}$ to $A^{C14}$ each independently represents C—R or N. R represents a hydrogen atom or a substituent. $L^{C1}$ represents a single bond or a divalent linking group.

The formula (C) will be described below.

$A^{C1}$ to $A^{C14}$ each independently represents C—R or N. R represents a hydrogen atom or a substituent. $A^{C1}$ to $A^{C6}$ are the same as $A^{B1}$ to $A^{B6}$ in the foregoing formula (B), and a preferred scope thereof are also the same as described there.

Regarding $A^{C7}$ to $A^{C14}$, the number of N (nitrogen atom) among $A^{C7}$ to $A^{C10}$ and the number of N among $A^{C11}$ to $A^{C14}$ each is preferably from 0 to 2, more preferably from 0 to 1. Members representing N are selected from among $A^{C8}$ to $A^{C10}$ and among $C_{A12}$ to $A^{C14}$, more preferably from among $A^{C8}$, $A^{C9}$, $A^{C12}$, and $A^{C13}$, particularly preferably from among $A^{C8}$ and $A^{C12}$.

In the case where $A^{C7}$ to $A^{C14}$ each represents C—R, $R^{C8}$ in each of $A^{C12}$ is preferably a hydrogen atom, an alkyl group, a polyfluoroalkyl group, an aryl group, an amino group, an alkoxy group, an aryloxy group, a fluorine atom or a cyano group; more preferably a hydrogen atom, a polyfluoroalkyl group, an alkyl group, an aryl group, a fluorine atom or a cyano group; and particularly preferably a hydrogen atom, a polyfluoroalkyl group or a cyano group. R in each of $A^{C7}$, $A^{C9}$, $A^{C11}$, and $A^{C13}$ is preferably a hydrogen atom, an alkyl group, a polyfluoroalkyl group, an aryl group, an amino group, an alkoxy group, an aryloxy group, a fluorine atom or a cyano group; more preferably a hydrogen atom, a polyfluoroalkyl group, a fluorine atom or a cyano group; and particularly preferably a hydrogen atom or a fluorine atom. R in each of by $A^{C7}$ and $A^{C9}$ is preferably a hydrogen atom or a fluorine atom, more preferably a hydrogen atom. In the case where any two of $A^{C7}$ to $A^{C9}$ and $A^{C11}$ to $A^{C13}$ represent C—R, Rs may be connected to each other to form a ring.

The linking group represented by $L^{C1}$ is the same as the linking group represented by $L^{B1}$ in the foregoing formula (B), and a preferred scope thereof is also the same as described there.

The Pt complex represented by the formula (B) is more preferably a Pt complex represented by the following formula (D).

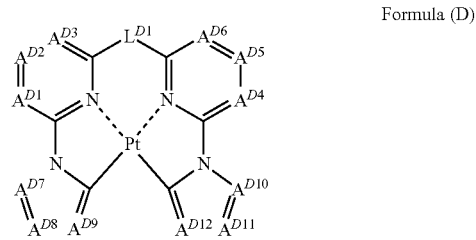

Formula (D)

In the formula (D), $A^{D1}$ to $A^{D12}$ each independently represents C—R or N. R represents a hydrogen atom or a substituent. $L^{D1}$ represents a single bond or a divalent linking group.

The formula (D) will be described below.

$A^{D1}$ to $A^{D12}$ each independently represents C—R or N. R represents a hydrogen atom or a substituent.

$A^{D1}$ to $A^{D6}$ are the same as $A^{B1}$ to $A^{B6}$ in the foregoing formula (B), and a preferred scope thereof is also the same as described there.

Regarding $A^{D7}$ to $A^{D12}$, the number of N (nitrogen atom) among $A^{D7}$ to $A^{D9}$ and the number of N among $A^{D10}$ to $A^{D12}$ each is preferably from 0 to 2, more preferably from 0 to 1, particularly preferably 1. Members representing N are selected from among $A^{D7}$ to $A^{D9}$ and among $A^{D10}$ to $A^{D12}$, more preferably from among $A^{D7}$, $A^{D9}$, $A^{D10}$, and $D^{12}$, particularly preferably from among $A^{D7}$ and $A^{D10}$.

In the case where $A^{D7}$ to $A^{D12}$ each represents C—R, R represented by $A^{D8}$ and $A^{D11}$ is preferably a hydrogen atom, an alkyl group, a polyfluoroalkyl group, an aryl group, an amino group, an alkoxy group, an aryloxy group, a fluorine atom or a cyano group; more preferably a hydrogen atom, a polyfluoroalkyl group, an alkyl group, an aryl group, a fluorine atom or a cyano group; and particularly preferably a polyfluoroalkyl group (e.g., a trifluoromethyl group or a perfluoroethyl group) or a cyano group. R in each of $A^{D7}$, $A^{D9}$, $A^{D10}$, and $A^{D12}$ is preferably a hydrogen atom, an alkyl group, a polyfluoroalkyl group, an aryl group, an amino group, an alkoxy group, an aryloxy group, a fluorine atom or a cyano group; more preferably a hydrogen atom, a hydrogen atom or a fluorine atom; and particularly preferably a hydrogen atom. In the case where any two of $A^{D7}$ to $A^{D12}$ represent C—R, Rs may be connected to each other to form a ring.

The linking group represented by $L^{D1}$ is the same as the linking group represented by $L^{B1}$ in the foregoing formula (B), and a preferred scope thereof is also the same as described there.

One of more preferred examples of the platinum complex phosphorescent material having a tetradentate ligand is a Pt complex represented by the following formula (E).

Formula (E)

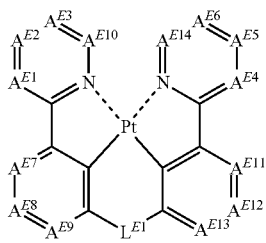

In the formula (E), $A^{E1}$ to $A^{E14}$ each independently represents C—R or N. R represents a hydrogen atom or a substituent. $L^{E1}$ represents a single bond or a divalent linking group.

The formula (E) will be described below.

$A^{E1}$ to $A^{E12}$ each independently represents C—R or N. R represents a hydrogen atom or a substituent. $A^{E1}$ to $A^{E6}$ are the same as $A^{B1}$ to $A^{B6}$ in the foregoing formula (B), and a preferred scope thereof is also the same as described there. $A^{E7}$ to $A^{E14}$ are the same as $A^{C7}$ to $A^{C14}$ in the foregoing formula (C), and a preferred scope thereof is also the same as described there.

The linking group represented by $L^{E1}$ is the same as the linking group represented by $L^{B1}$ in the foregoing formula (B).

$L^{E1}$ represents preferably a single bond, an alkylene group, an arylene group, a heteroarylene group, an imino group, an oxy group, a thio group or a silylene group; more preferably an alkylene group, an imino group, an oxy group, a thio group or a silylene group; still more preferably an alkylene group; still more preferably a methylene group; still more preferably a di-substituted methylene group; still more preferably a dimethylmethylene group, a diethylmethylene group, a diisobutylmethylene group, a dibenzylmethylene group, an ethylmethylmethylene group, a methylpropylmethylene group, an isobutylmethylmethylene group, a diphenylmethylene group, a methylphenylmethylene group, a cyclohexanediyl group, a cyclopentanediyl group, a fluorenediyl group or a fluoromethylmethylene group; and particularly preferably a dimethylmethylene group, a diphenylmethylene group or a cyclohexanediyl group.

One of more preferred examples of the platinum complex phosphorescent material having a tetradentate ligand is a Pt complex represented by the following formula (F).

Formula (F)

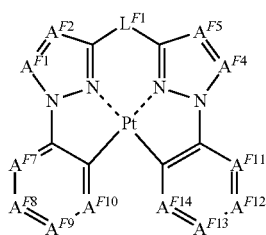

In the formula (F), $A^{F1}$ to $A^{F14}$ each independently represents C—R or N. R represents a hydrogen atom or a substituent. $L^{F1}$ represents a single bond or a divalent linking group.

The formula (F) will be described below.

$A^{F1}$ to $A^{F14}$ each independently represents C—R or N. R represents a hydrogen atom or a substituent. $A^{F1}$ to $A^{F5}$ are the same as $A^{B1}$ to $A^{B5}$ in the foregoing formula (B). $A^{F1}$ to $A^{F5}$ each is preferably C—R, and Rs may be connected to each other to form a ring. In the case where $A^{F1}$ to $A^{F5}$ each is C—R, R in each of $A^{F1}$ to $A^{F5}$ is preferably a hydrogen atom, an alkyl group, an aryl group, an amino group, an alkoxy group, an aryloxy group, a fluorine atom or a cyano group; more preferably a hydrogen atom, an aryl group, a fluorine atom or a cyano group; particularly preferably a hydrogen atom.

$A^{F7}$ to $A^{F14}$ are the same as $A^{C7}$ to $A^{C14}$ in the foregoing formula (C), and a preferred scope thereof is also the same as described there. In particular, in the case where any two of $A^{C7}$ to $A^{C9}$ and $A^{C11}$ to $A^{C13}$ represent C—R, the ring structure formed by Rs connected to each other is preferably a furan ring, a benzofuran ring, a pyrrole ring, a benzopyrrole ring, a thiophene ring, a benzothiophene ring or a fluorine ring. These rings may further have a substituent.

The linking group represented by $L^{F1}$ is the same as the linking group represented by $L^{B1}$ in the foregoing formula (B), and a preferred scope thereof is also the same.

Specific examples of the light-emitting materials are illustrated below which, however, are not to be construed to limit the invention in any way.

D-1

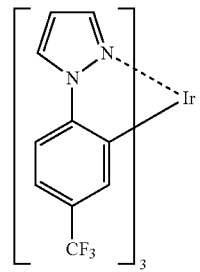

D-2

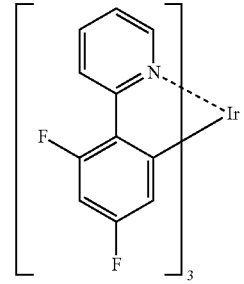

D-3

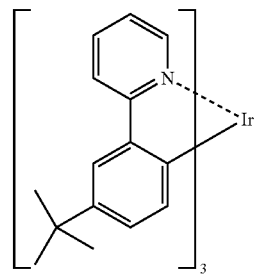

D-4

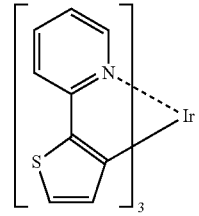

D-5 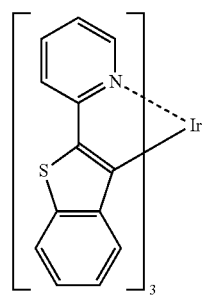
D-6 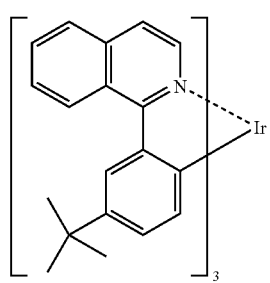
D-7 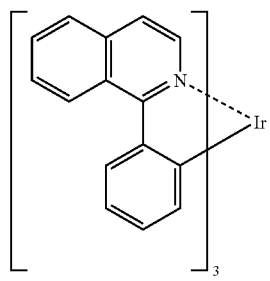
D-8 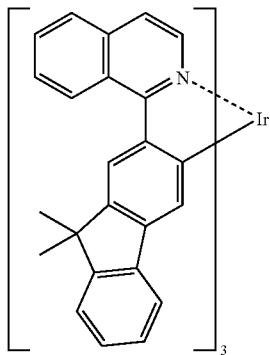
D-9 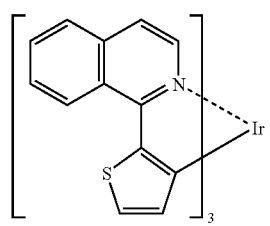
D-10 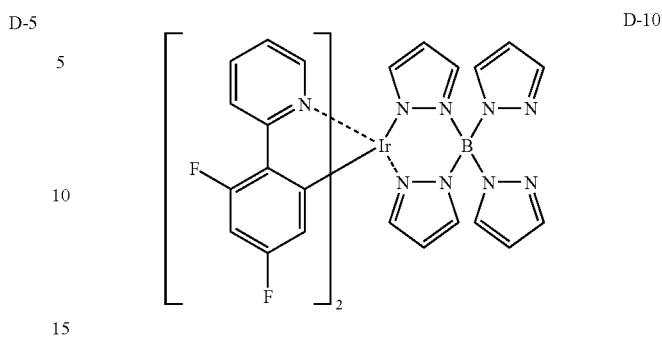
D-11 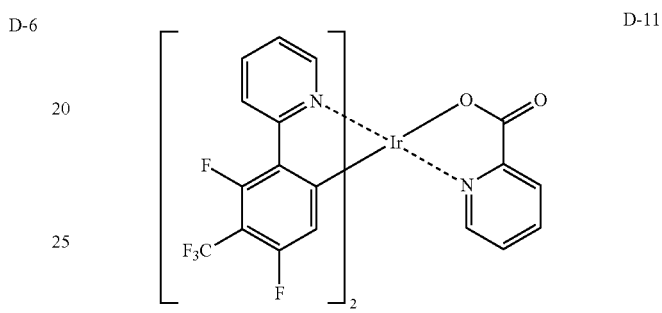
D-12 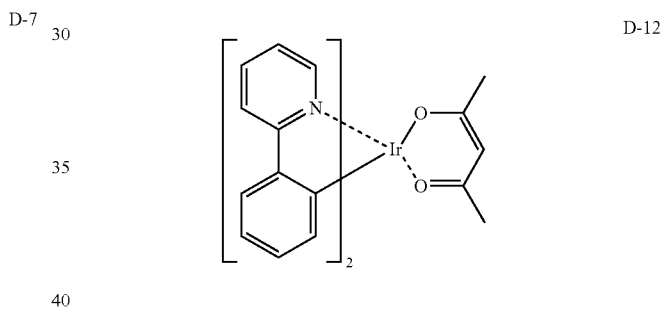
D-13 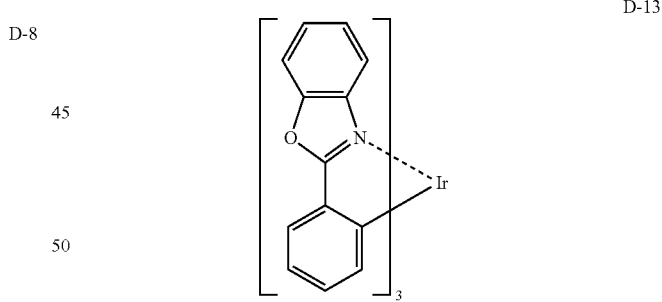
D-14 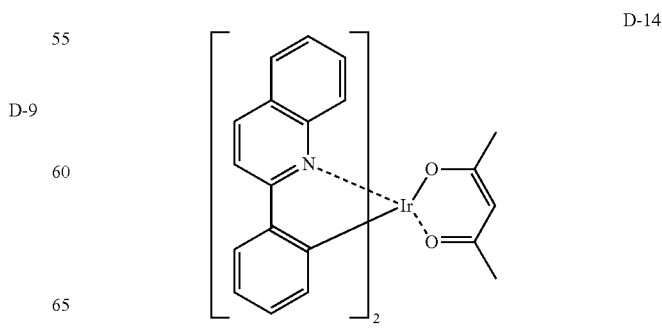

-continued
D-15
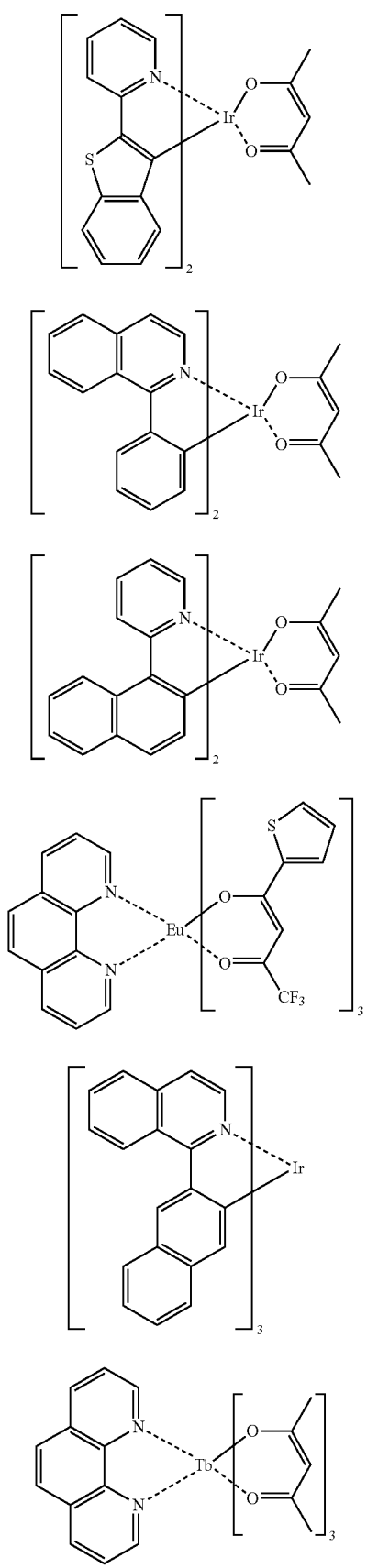
D-16
D-17
D-18
D-19
D-20
-continued
D-21
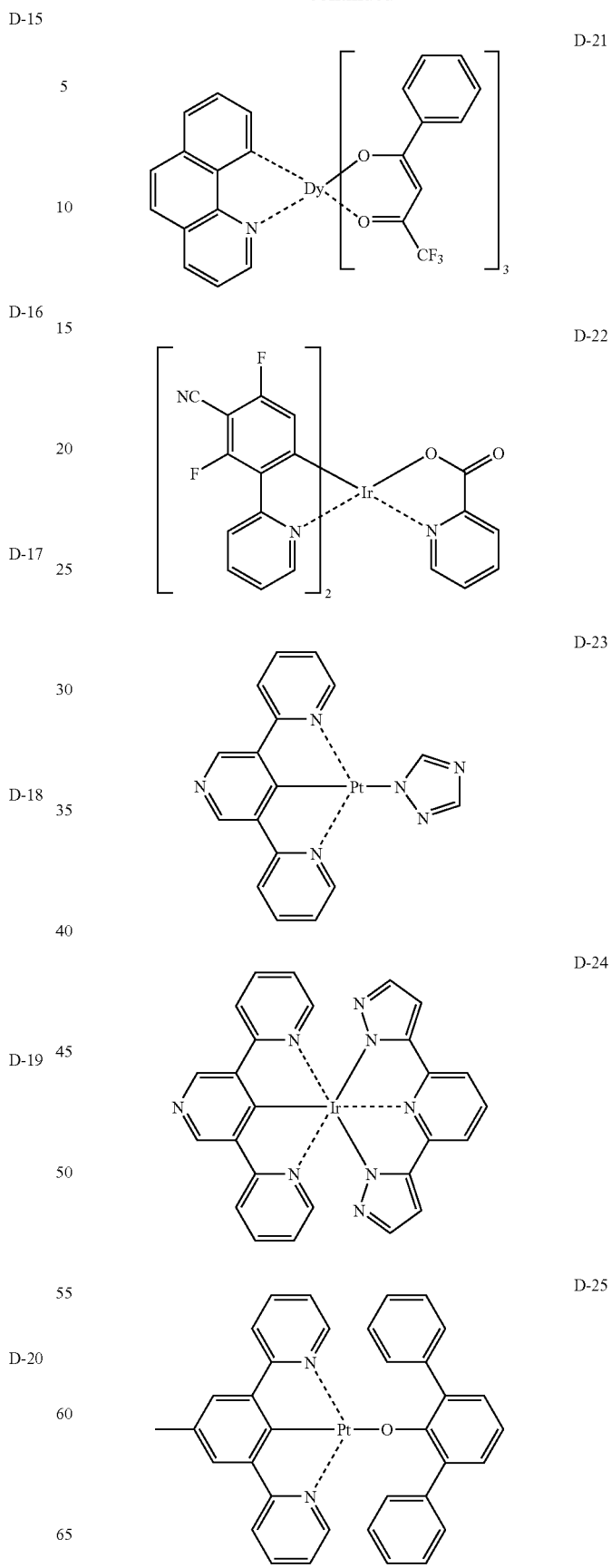
D-22
D-23
D-24
D-25

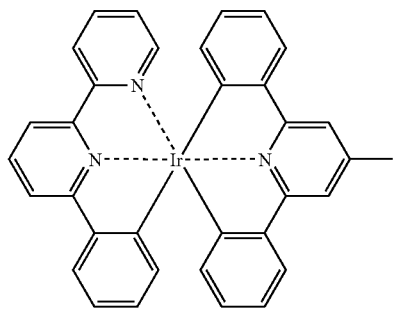 D-26
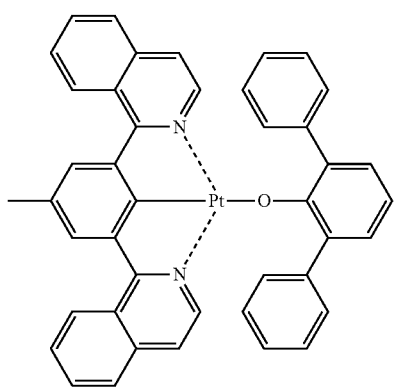 D-27
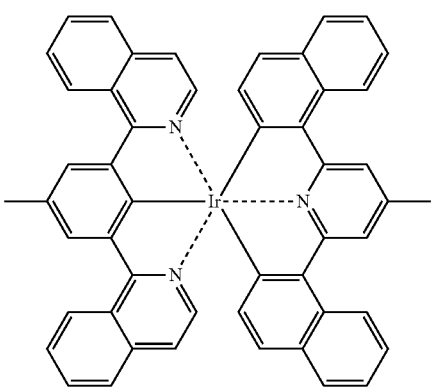 D-28
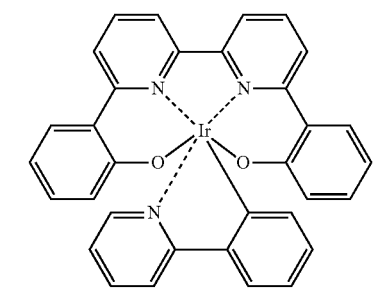 D-29
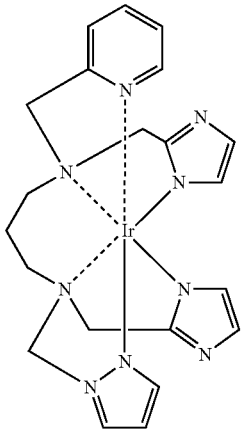 D-30
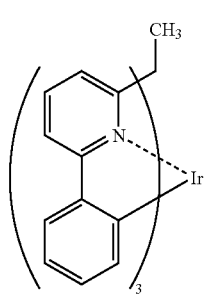 D-31
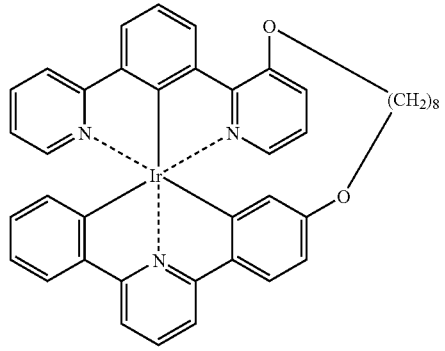 D-32
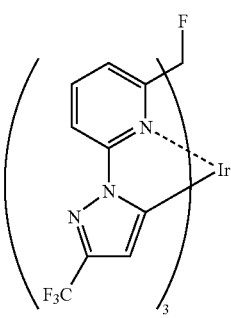 D-33

D-34
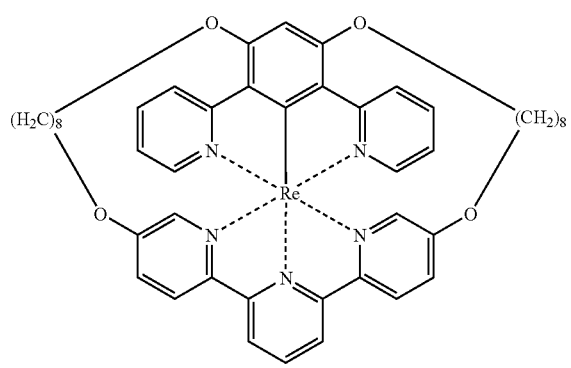
1-3
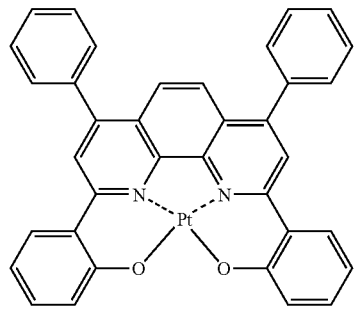
D-35
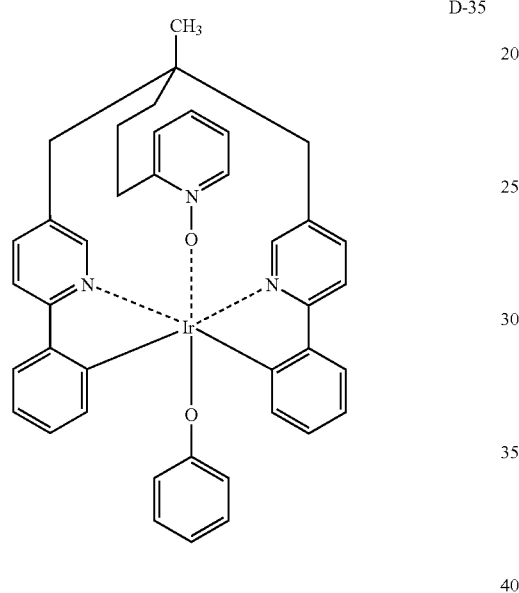
2-1
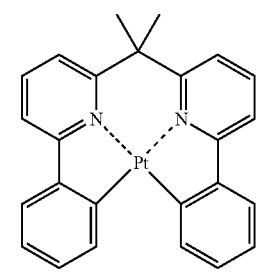
2-2
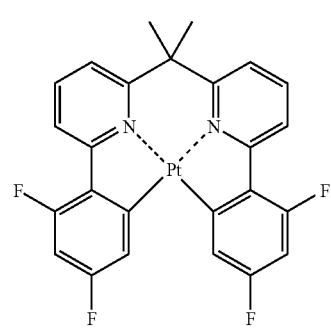
Also, examples of the platinum complex capable of emitting phosphorescence and containing a tetradentate ligand are illustrated below which, however, are not limitative at all.
2-3
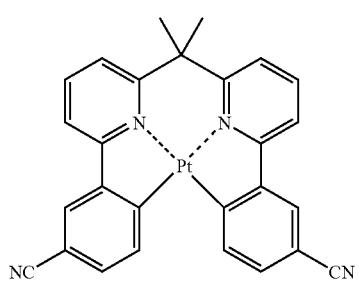
1-1
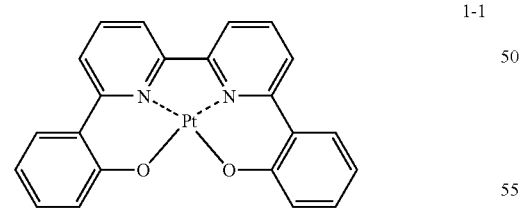
1-2
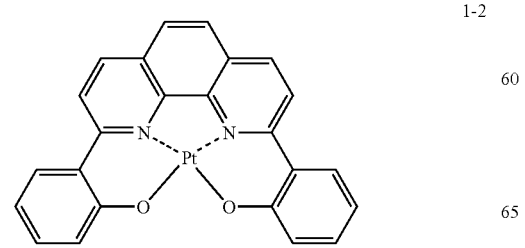
2-4
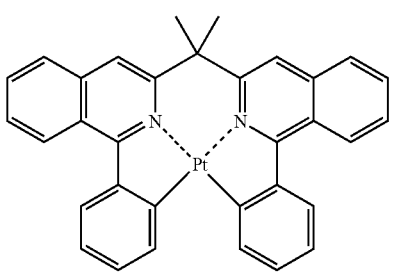

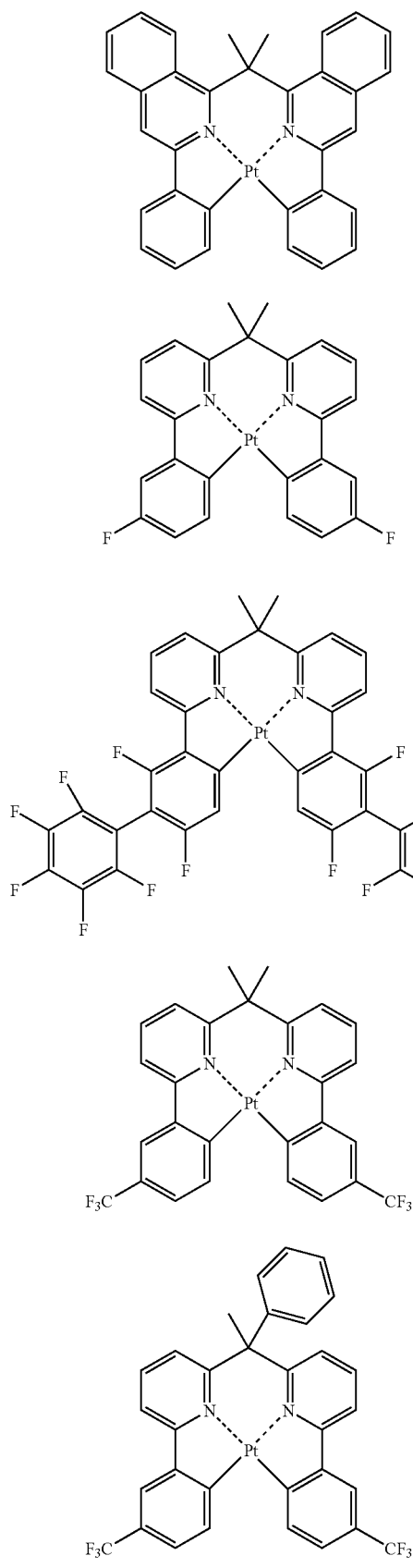
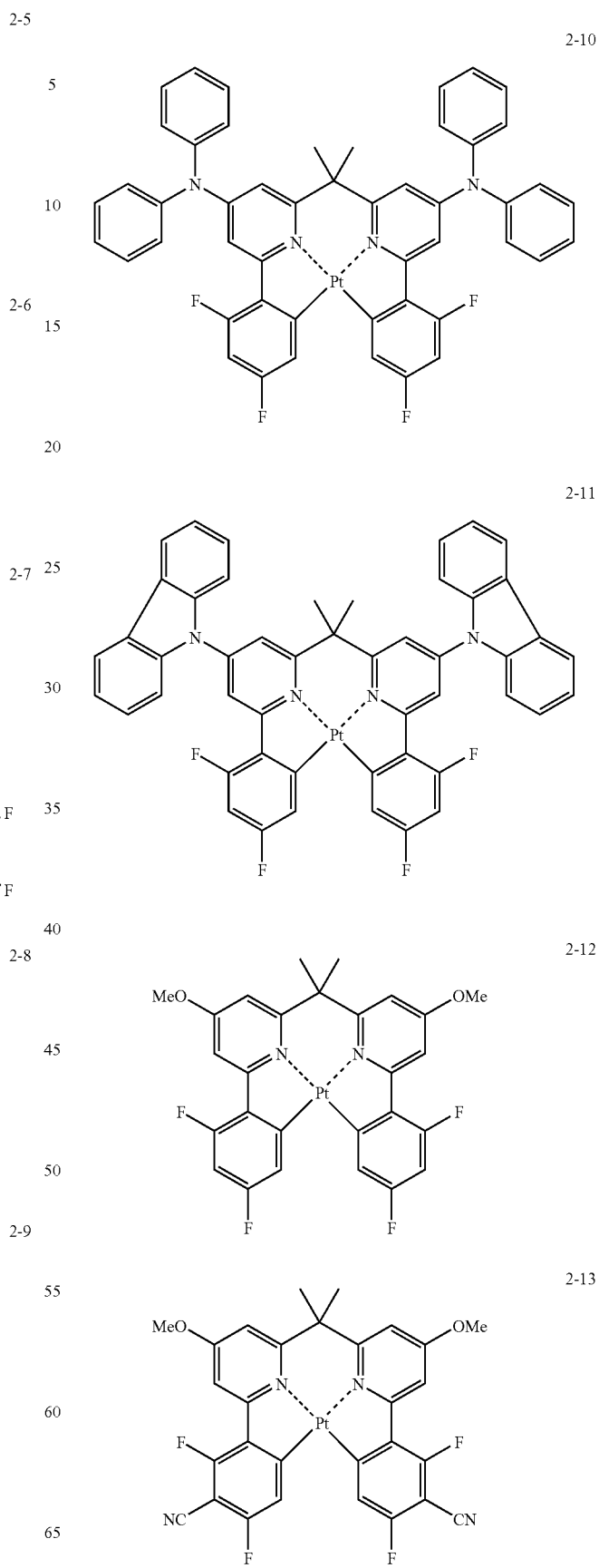

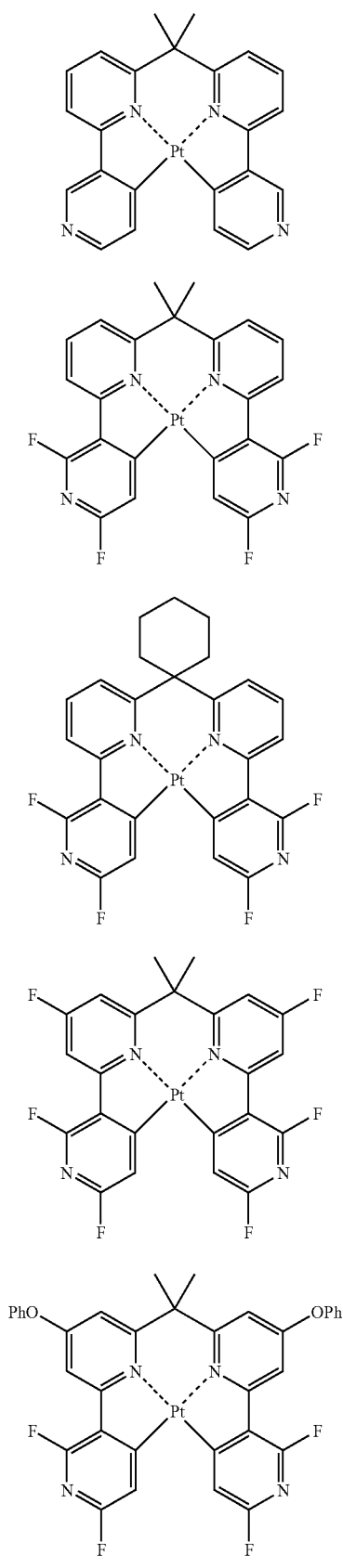
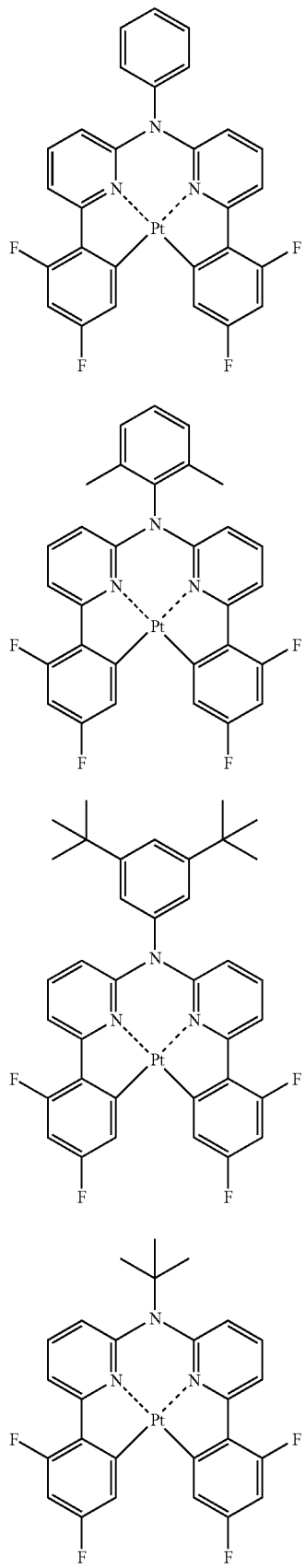

4-5
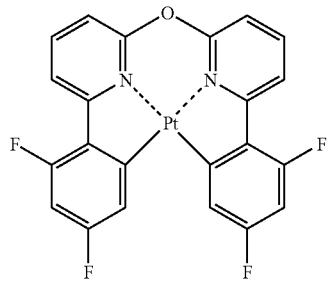
5-1
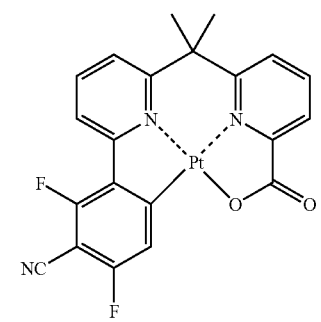
5-2
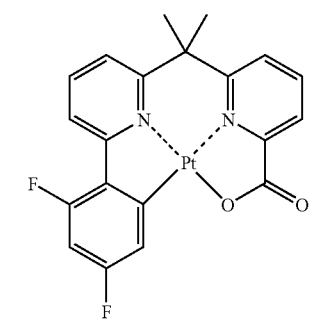
5-3
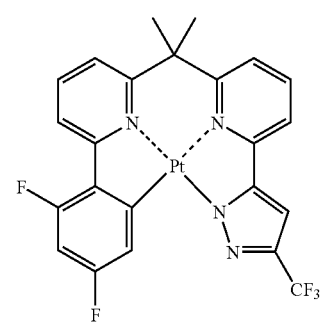
5-4
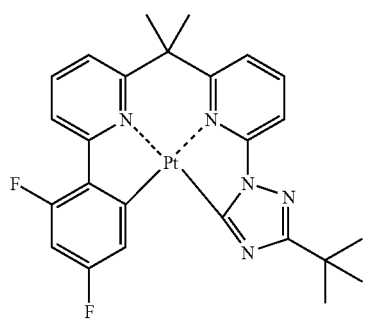
6-1
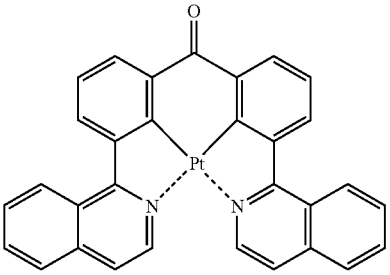
6-2
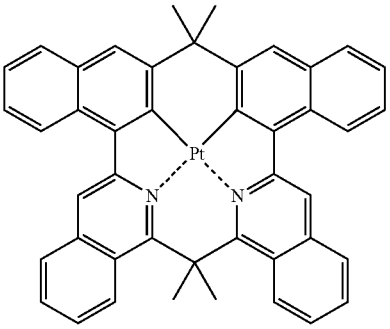
6-3
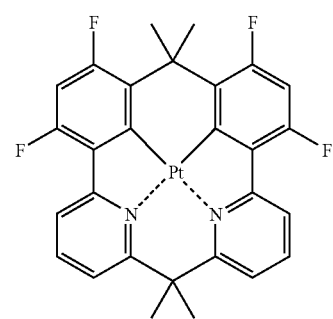
6-4
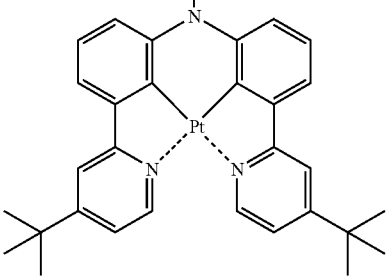
6-5
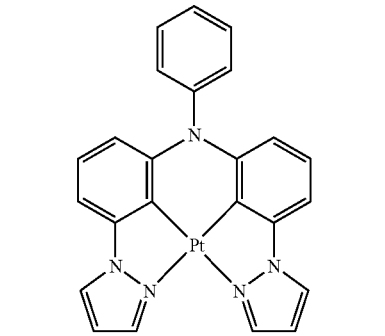

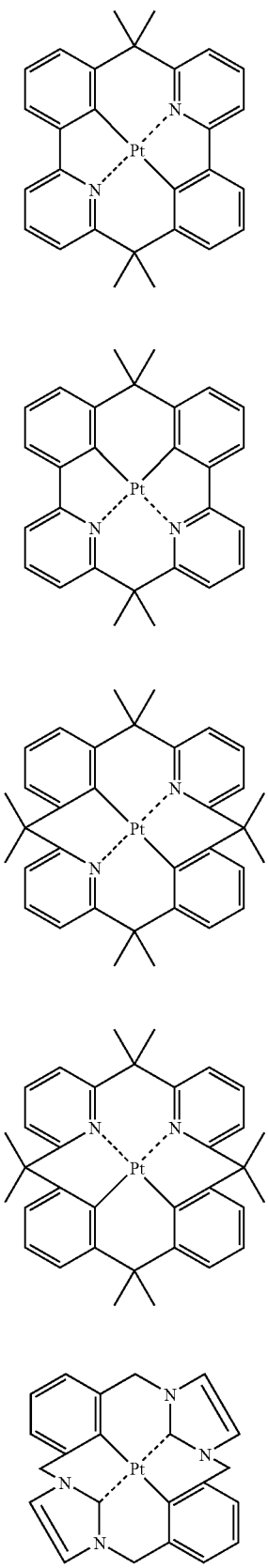
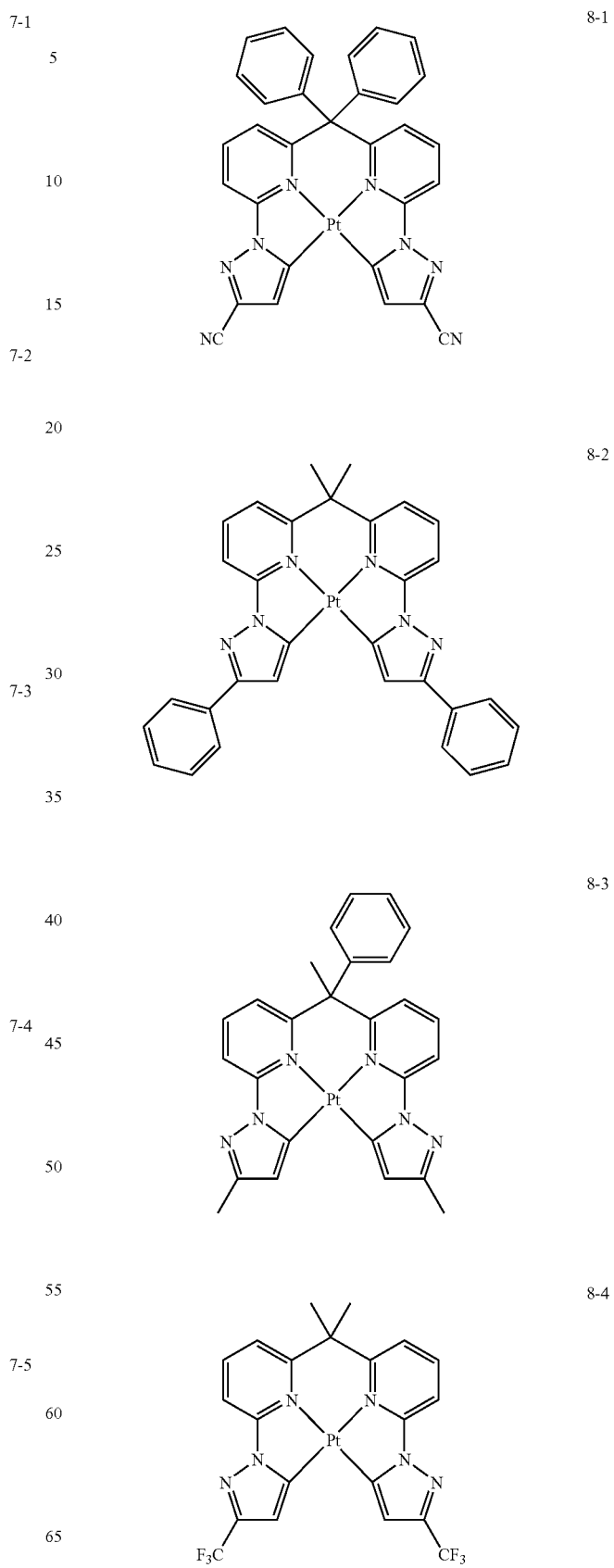

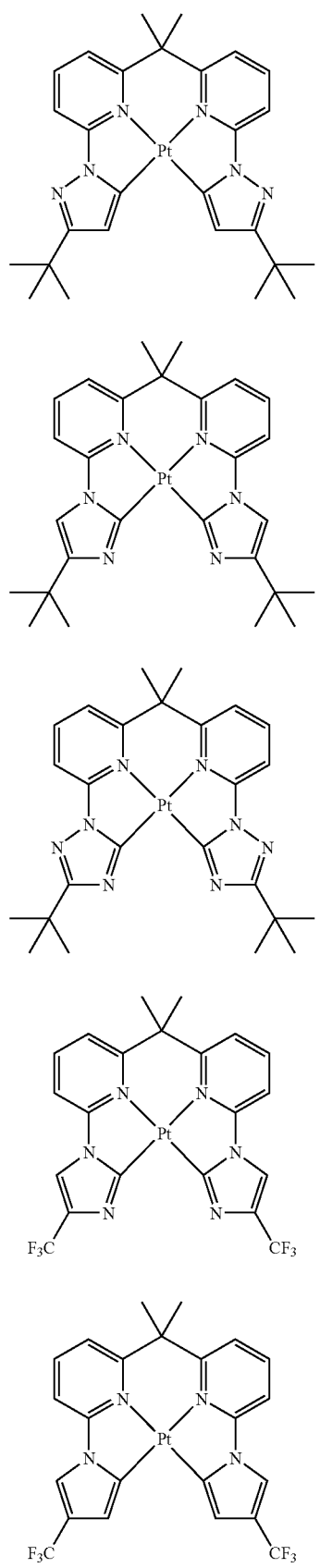
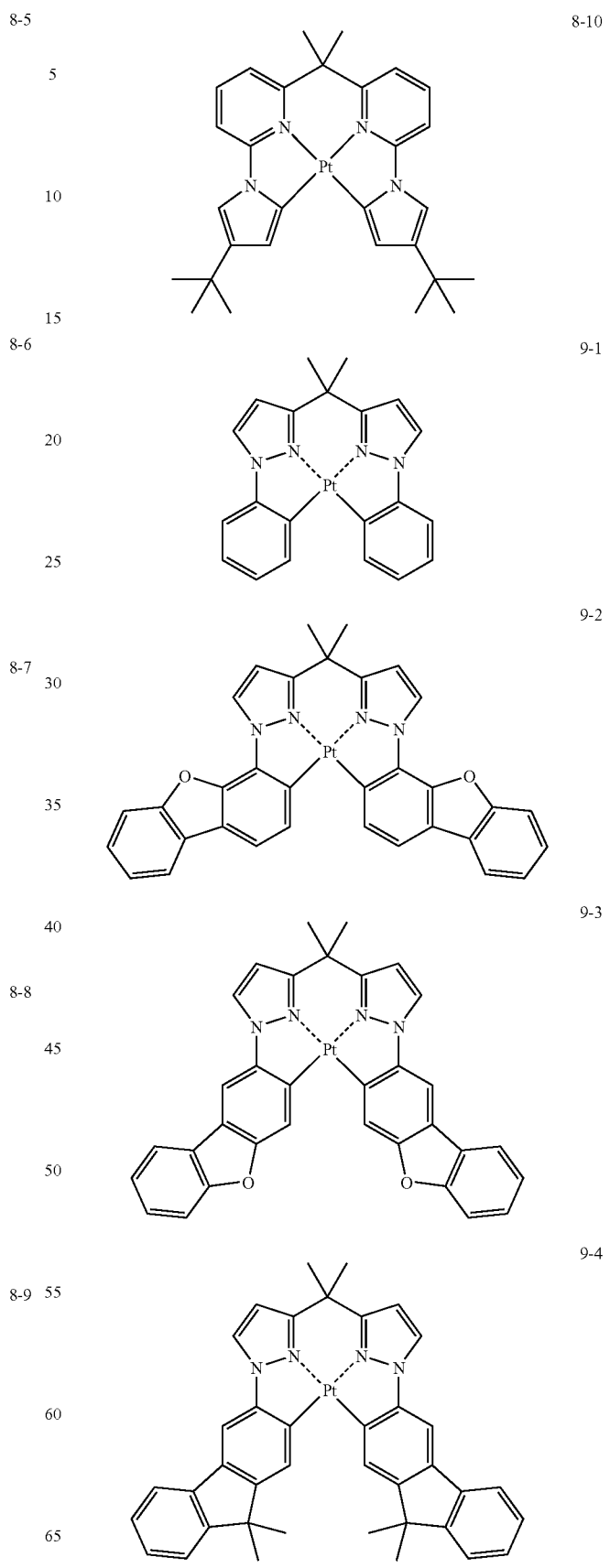

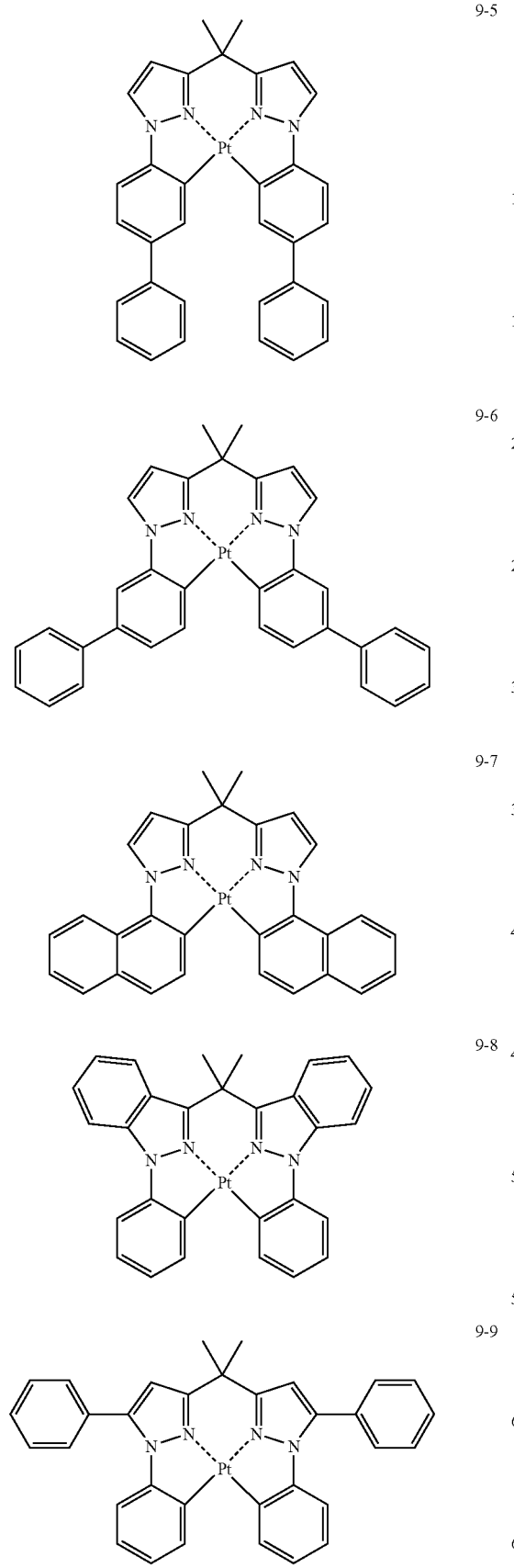
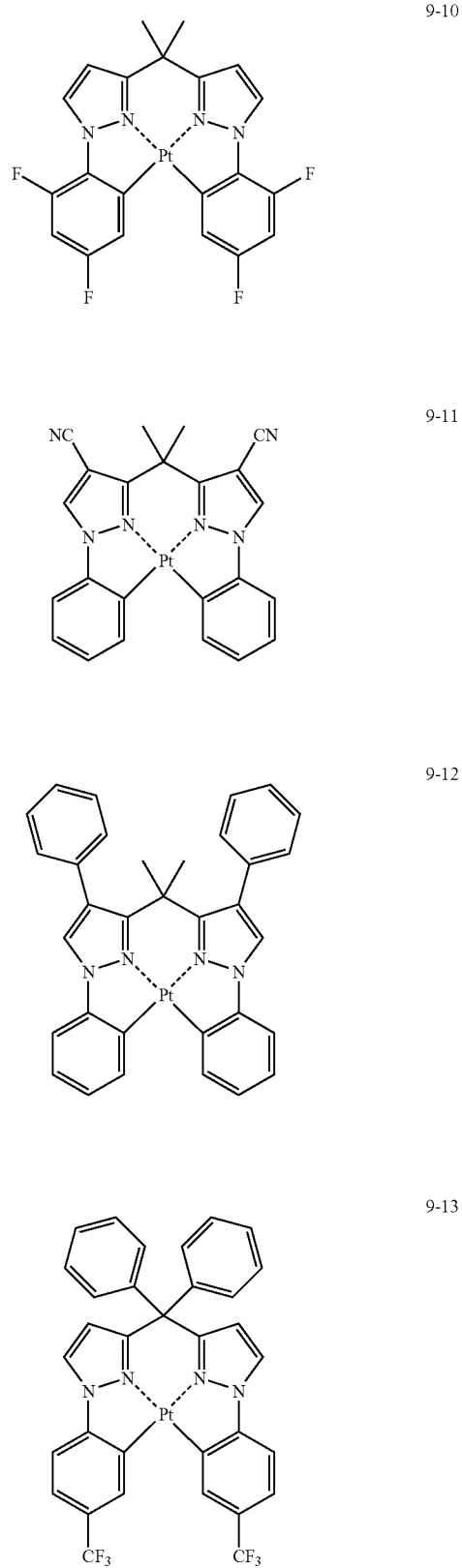

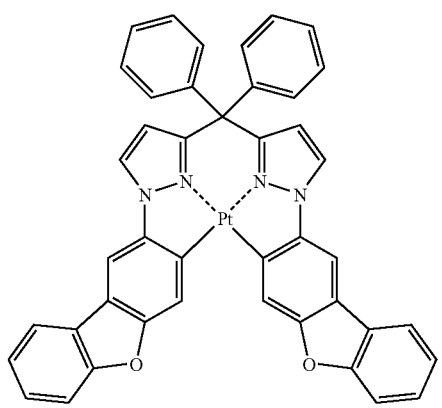

9-14

The light-emitting material is incorporated in the light-emitting layer in an amount of generally from 0.1 to 50% by weight (% by mass) based on the weight of all the compounds forming the light-emitting layer and, in view of durability and external quantum efficiency, in an amount of preferably from 1 to 50% by weight, more preferably from 2 to 40% by weight.

(Host Material)

The term "host material" as used herein means a material constituting the light-emitting layer excluding light-emitting materials and having at least one function among a function of dispersing light-emitting materials to hold them in the light-emitting layer, a function of receiving a hole from anode or from a hole transporting layer, a function of receiving an electron from cathode or from an electron transporting layer, a function of transporting a hole and/or an electron, a function of providing a site for recombination of hole and electron, a function of transferring energy of exciton generated by the recombination to a light-emitting material, and a function of transporting a hole and/or an electron to a light-emitting material.

As host materials to be contained in a light-emitting layer of the invention, e.g., materials having a carbazole skeleton, having a azacabazole skeleton, having an indole skelton, having an azaindole skeleton, having a diarylamine skeleton, having a pyridine skeleton, having a pyrazine skeleton, having a triazine skeleton, and having an arylsilane skeleton, and those described later in the items of a hole injecting layer, a hole transporting layer, an electron injecting layer, and an electron transporting layer are exemplified.

The light-emitting layer may contain two or more host materials. As to kinds of the hosts, it is more preferred to select two members from among the compounds represented by formula (1), metal complex host materials, aromatic hydrocarbon host materials, and nitrogen-containing organic host materials. It is still more preferred to incorporate any one of the metal complex host materials, aromatic hydrocarbon host materials, and nitrogen-containing organic host materials in addition to the compound represented by formula (1).

The metal complex host materials are host materials including metal complexes. Metal atoms constituting the metal complexes are not particularly limited. However, 2-valent or 3-valent metal atoms are preferred, 3-valent aluminum atom, 2-valent zinc atom, 3-valent gallium atom, 2-valent beryllium atom, and 2-valent magnesium atom are more preferred, 3-valent aluminum atom, 3-valent gallium atom, and 2-valent zinc atom are still more preferred, and 3-valent aluminum atom is particularly preferred.

The aromatic hydrocarbon host materials are host materials including organic materials that contain an aromatic ring or rings constituted by only carbon and hydrogen, with the aromatic rings optionally having a substituent or substituents. The aromatic hydrocarbon host materials preferably do not have a condensed ring structure such as naphthalene ring.

The nitrogen-containing organic materials are host materials that contain organic compounds having a nitrogen atom or atoms, and examples thereof include nitrogen-containing heterocyclic compounds and metal complexes containing them as ligands. The nitrogen-containing organic materials are preferably nitrogen-containing heterocyclic compounds and metal complexes containing them as ligands, more preferably compounds having a 5-membered nitrogen-containing hetero ring (pyrrole ring, pyrazole ring, imidazole ring or triazole ring, preferably pyrrole ring or imidazole ring, more preferably pyrrole ring), still more preferably compounds having a condensed skeleton in which a 5-membered nitrogen-containing ring is condensed with a 6-membered ring.

Ionization potential of the host material contained in the light-emitting layer is preferably from 5.8 eV to 6.3 eV, more preferably from 5.95 to 6.25 eV, still more preferably from 6.0 to 6.2 eV.

The electron mobility of the host material in the light-emitting layer is from $1\times10^{-6}$ to $1\times10^{-1}$ cm$^2$/Vs, more preferably from $5\times10^{-6}$ cm$^2$/Vs to $1\times10^{-2}$ cm$^2$/Vs, still more preferably from $1\times10^{-5}$ to $1\times10^{-2}$ cm$^2$/Vs, particularly preferably from $5\times10^{-5}$ to $1\times10^{-2}$ cm$^2$/Vs.

The hole mobility of the host material in the light-emitting layer is from $1\times10^{-6}$ to $1\times10^{-1}$ cm$^2$/Vs, more preferably from $5\times10^{-6}$ cm$^2$/Vs to $1\times10^{-2}$ cm$^2$/Vs, still more preferably from $1\times10^{-5}$ to $1\times10^{-2}$ cm$^2$/Vs, particularly preferably from $5\times10^{-5}$ to $1\times10^{-2}$ cm$^2$/Vs.

The glass transition point of a host material contained in the light-emitting layer is preferably from 90 to 400° C., more preferably from 100 to 380° C., still more preferably from 120 to 370° C., and especially preferably from 140 to 360° C.

The $T_1$ level (the energy level in the state of minimum triplet excitation) of the light-emitting material contained in the light-emitting layer containing at least a platinum complex is preferably 60 kcal/mol or more (251.4 kJ/mol or more) and 90 kcal/mol or less (377.1 kJ/mol or less), more preferably 62 kcal/mol or more (259.78 kJ/mol or more) and 85 kcal/mol or less (356.15 kJ/mol or less), and still more preferably 65 Kcal/mol or more (272.35 kJ/mol or more) and 80 Kcal/mol or less (335.2 kJ/mol or less).

The $T_1$ level (the energy level in the state of minimum triplet excitation) of the host material contained in the light-emitting layer is preferably 60 kcal/mol or more (251.4 kJ/mol or more) and 90 kcal/mol or less (377.1 kJ/mol or less), more preferably 62 kcal/mol or more (259.78 kJ/mol or more) and 85 kcal/mol or less (356.15 kJ/mol or less), and still more preferably 65 kcal/mol or more (272.35 kJ/mol or more) and 80 kcal/mol or less (335.2 kJ/mol or less).

$T_1$ level (the energy level in the state of minimum triplet excitation) of a layer contiguous to the light-emitting layer (a hole transporting layer, an electron transporting layer, a charge blocking layer, an exciton blocking layer, or the like) is preferably 60 kcal/mol or more (251.4 kJ/mol or more) and 90 kcal/mol or less (377.1 kJ/mol or less), more preferably 62 kcal/mol or more (259.78 kJ/mol or more) and 85 kcal/mol or less (356.15 kJ/mol or less), still more preferably 65 kcal/mol or more (272.35 kJ/mol or more) and 80 kcal/mol or less (335.2 kJ/mol or less).

The thickness of the light-emitting layer is not particularly limited, but is usually preferably from 2 to 500 nm, and in view of external quantum efficiency, the thickness is more preferably from 3 to 200 nm, still more preferably from 5 to 100 nm.

(Hole Injecting Layer and Hole Transporting Layer)

The hole injecting layer and the hole transporting layer are layers having a function to receive holes from the anode or anode side and transport the holes to the cathode side. The hole injecting layer and the hole transporting layer are specifically preferably the layers containing carbazole derivatives, azacarbazole derivatives, indole derivatives, azaindole derivatives, triazole derivatives, oxazole derivatives, oxadiazole derivatives, imidazole derivatives, polyarylalkane derivatives, pyrazoline derivatives, pyrazolone derivatives, phenylenediamine derivatives, arylamine derivatives, amino-substituted chalcone derivatives, styrylanthracene derivatives, fluorenone derivatives, hydrazone derivatives, stilbene derivatives, silazane derivatives, aromatic tertiary amine compounds, styrylamine compounds, aromatic dimethylidyne compounds, porphyrin compounds, organic silane derivatives, carbon, and various kinds of metal complexes represented by Ir complex, having phenylazole, or phenylazine as the ligand.

The glass transition point of each of the hole injecting layer and the hole transporting layer is preferably in the same range as the glass transition point of the host material for the aforesaid light-emitting layer.

The thickness of the hole injecting layer and hole transporting layer is preferably 500 nm or less from the viewpoint of lowering driving voltage.

The thickness of the hole transporting layer is preferably from 1 to 500 nm, more preferably from 5 to 200 nm, and still more preferably from 10 to 100 nm. The thickness of the hole injecting layer is preferably from 0.1 to 200 nm, more preferably from 0.5 to 100 nm, and still more preferably from 1 to 100 nm.

The hole injecting layer and the hole transporting layer may be a single layer structure including one or two or more of the above materials, or may be a multilayer including comprising a plurality of layers of the same or different compositions.

(Electron Injecting Layer and Electron Transporting Layer)

The electron injecting layer and the electron transporting layer are layers having a function to receive electrons from the cathode or cathode side and transport the electrons to the anode side. The electron injecting layer and the electron transporting layer are specifically preferably layers containing triazole derivatives, oxazole derivatives, oxadiazole derivatives, imidazole derivatives, fluorenone derivatives, anthraquinodimethane derivatives, anthrone derivatives, diphenylquinone derivatives, thiopyran dioxide derivatives, carbodiimide derivatives, fluorenylidenemethane derivatives, distyrylpyrazine derivatives, tetracarboxylic anhydride of aromatic rings such as naphthalene, 1,3,5-triphenylbenzen derivatives, perylene, etc., a phthalocyanine derivative, various metal complexes represented by metal complexes of 8-quinolinol derivatives or metalphthalocyanine and metal complexes having benzoxazole, benzothiazole as the ligand, and organic silane derivative, etc.

The glass transition point of each of the electron injecting layer and the electron transporting layer is preferably in the same range as the glass transition point of the host material for the aforesaid light-emitting layer.

The electron transporting material preferably contains a metal complex material. By containing a metal complex material in the electron transporting material, advantages of the invention such as lowering driving voltage and improving luminance efficiency can be enhanced.

Metal atoms constituting the metal complexes are not particularly limited. However, 2-valent or 3-valent metal atoms are preferred, 3-valent aluminum atom, 2-valent zinc atom, 3-valent gallium atom, 2-valent beryllium atom, and 2-valent magnesium atom are more preferred, 3-valent aluminum atom, 3-valent gallium atom, and 2-valent zinc atom are still more preferred, and 3-valent aluminum atom is particularly preferred.

The thickness of each of the electron injecting layer and electron transporting layer is preferably 500 nm or less from the viewpoint of lowering driving voltage.

The thickness of the electron transporting layer is preferably from 1 to 500 nm, more preferably from 5 to 200 nm, and still more preferably from 10 to 100 nm. The thickness of the electron injecting layer is preferably from 0.1 to 200 nm, more preferably from 0.2 to 100 nm, and still more preferably from 0.5 to 50 nm.

The electron injecting layer and the electron transporting layer may be a single layer structure comprising one or two or more of the above materials, or may be a multilayer structure comprising a plurality of layers of the same or different compositions.

(Hole Blocking Layer)

A hole blocking layer is a layer having a function of preventing holes transported from the anode side to the light-emitting layer from passing through to the cathode side. In the invention, a hole blocking layer can be provided as an organic layer contiguous to the light-emitting layer on the cathode side.

As the examples of the organic compounds constituting the hole blocking layer, aluminum complexes, e.g., BAlq, etc., triazole derivatives, phenanthroline derivatives, e.g., BCP, etc., can be exemplified.

The thickness of the hole blocking layer is preferably from 1 to 500 nm, more preferably from 5 to 200 nm, and still more preferably from 10 to 100 nm.

The hole blocking layer may be a single layer structure comprising one or two or more of the above materials, or may be a multilayer structure comprising a plurality of layers of the same or different compositions.

Constituents of an organic electroluminescent device of the invention, other than organic layers, are described in detail below.

(Substrate)

A substrate for use in the invention is preferably a substrate that does not scatter or attenuate the light emitted from the organic layer. The specific examples of the materials of the substrate include inorganic materials, e.g., yttria stabilized zirconia (YSZ), glass, etc., and organic materials, such as polyester, e.g., polyethylene terephthalate, polybutylene phthalate, polyethylene naphthalate, etc., polystyrene, polycarbonate, polyether sulfone, polyallylate, polyimide, polycycloolefin, norbornene resin, poly(chloro-trifluoroethylene), etc.

When glass is used as a substrate, non-alkali glass is preferably used as the material for reducing elution of ions from the glass. Further, when soda lime glass is used, it is preferred to provide a barrier coat such as silica. In the case of organic materials, materials excellent in heat resistance, dimensional stability, solvent resistance, electrical insulating properties and processability are preferably used.

The form, structure and size of a substrate are not especially restricted, and these can be arbitrarily selected in accordance with the intended use and purpose of the light-emitting device. In general, a substrate is preferably in a plate-like form. The structure of a substrate may be a single layer structure or may be a layered structure, and may consist of a single member or may be formed of two or more members.

A substrate may be colorless and transparent, or may be colored and transparent, but from the point of not scattering or attenuating the light emitted from the light-emitting layer, a colorless and transparent substrate is preferably used.

A substrate can be provided with a moisture permeation preventing layer (a gas barrier layer) on the front surface or rear surface.

As the materials of the moisture permeation preventing layer (the gas barrier layer), inorganic materials such as silicon nitride and silicon oxide are preferably used. The moisture permeation preventing layer (the gas barrier layer) can be formed, for example, by a high frequency sputtering method.

When a thermoplastic substrate is used, if necessary, a hard coat layer and an undercoat layer may further be provided.

(Electrode)
(Anode)

An anode is generally sufficient to have the function of the electrode to supply holes to an organic layer. The form, structure and size of an anode are not especially restricted, and these can be arbitrarily selected from known materials of electrode in accordance with the intended use and purpose of the light-emitting device. As described above, an anode is generally provided as a transparent anode.

As the materials of anode, for example, metals, alloys, metal oxides, electrically conductive compounds, and mixtures of these materials are preferably exemplified. The specific examples of the materials of anode include electrically conductive metal oxides, e.g., tin oxide doped with antimony or fluorine (ATO, FTO), tin oxide, zinc oxide, indium oxide, indium tin oxide (ITO), indium zinc oxide (IZO), etc., metals, e.g., gold, silver, chromium, nickel, etc., mixtures or layered products of these metals with electrically conductive metal oxides, inorganic electrically conductive substances, e.g., copper iodide, copper sulfide, etc., organic electrically conductive materials, e.g., polyaniline, polythiophene, polypyrrole, etc., layered products of these materials with ITO, etc. Of these materials, electrically conductive metal oxides are preferred, and ITO is especially preferred in view of productivity, high conductivity, transparency and the like.

An anode can be formed on the substrate in accordance with various methods arbitrarily selected from, for example, wet methods, e.g., a printing method, a coating method, etc., physical methods, e.g., a vacuum deposition method, a sputtering method, an ion plating method, etc., and chemical methods, e.g., a CVD method, a plasma CVD method, etc., taking the suitability with the material to be used in the anode into consideration. For example, in the case of selecting ITO as the material of an anode, the anode can be formed according to a direct current or high frequency sputtering method, a vacuum deposition method, an ion plating method, etc.

In an organic electroluminescent device of the invention, the position of the anode to be formed is not especially restricted and can be formed anywhere. The position can be arbitrarily selected in accordance with the intended use and purpose of the light-emitting device, but preferably provided on the substrate. In this case, the anode may be formed on the entire surface of one side of the substrate, or may be formed on a part of the organic layer.

As patterning in forming an anode, patterning may be performed by chemical etching such as by photo-lithography, may be carried out by physical etching such as by laser, may be performed by vacuum deposition or sputtering on a superposed mask, or a lift-off method and a printing method may be used.

The thickness of an anode can be optionally selected in accordance with the materials of the anode, so that cannot be regulated unconditionally, but the thickness is generally from 10 nm to 50 μm or so, and is preferably from 50 nm to 20 μm.

The value of resistance of an anode is preferably $10^3$ Ω/□ or less, and more preferably $10^2$ Ω/□ or less. In the case where an anode is transparent, the anode may be colorless and transparent, or colored and transparent. For the coupling out of luminescence from the transparent anode side, the transmittance is preferably 60% or more, and more preferably 70% or more.

In connection with transparent anodes, description is found in Yutaka Sawada supervised, Tomei Denkyoku-Maku no Shintenkai (New Development in Transparent Electrode Films), CMC Publishing Co., Ltd. (1999), and the description therein can be referred to. In the case of using a plastic substrate low in heat resistance, a transparent anode film-formed with ITO or IZO at a low temperature of 150° C. or less is preferred.

(Cathode)

A cathode is generally sufficient to have the function of the electrode to supply electrons to an organic layer. The form, structure and size of a cathode are not especially restricted, and these can be arbitrarily selected from known materials of electrode in accordance with the intended use and purpose of the light-emitting device.

As the materials of cathode, for example, metals, alloys, metal oxides, electrically conductive compounds, and mixtures of these materials are exemplified. The specific examples of the materials of cathode include alkali metals (e.g., Li, Na, K, Cs, etc.), alkaline earth metals (e.g., Mg, Ca, etc.), gold, silver, lead, aluminum, sodium-potassium alloy, lithium-aluminum alloy, magnesium-silver alloy, indium, rare earth metals, e.g., ytterbium, etc. These materials may be used by one kind alone, but from the viewpoint of the compatibility of stability and an electron injecting property, two or more kinds of materials are preferably used in combination.

As the materials constituting a cathode, alkali metals and alkaline earth metals are preferred of these materials in the point of electron injection, and materials mainly including aluminum are preferred for their excellent preservation stability.

The materials mainly including aluminum mean aluminum alone, alloys of aluminum with 0.01 to 10 mass % of alkali metal or alkaline earth metal, or mixtures of these (e.g., lithium-aluminum alloy, magnesium-aluminum alloy, etc.).

The materials of cathode are disclosed in JP-A-2-15595 and JP-A-5-121172, and the materials described in these patents can also be used in the invention.

A cathode can be formed by known methods with no particular restriction. For example, a cathode can be formed according to wet methods, e.g., a printing method, a coating method, etc., physical methods, e.g., a vacuum deposition method, a sputtering method, an ion plating method, etc., and chemical methods, e.g., a CVD method, a plasma CVD method, etc., taking the suitability with the material constituting the cathode into consideration. For example, in the case of selecting metals as the material of a cathode, the cathode can be formed with one or two or more kinds of materials at the same time or in order by sputtering, etc.

As patterning in forming a cathode, patterning may be performed by chemical etching such as by photo-lithography, may be carried out by physical etching such as by laser, may be performed by vacuum deposition or sputtering on a superposed mask, or a lift-off method and a printing method may be used.

The position of the cathode to be formed is not especially restricted and can be formed anywhere in the invention. The cathode may be formed on the entire surface of the organic layer, or may be formed on a part of the organic layer.

A dielectric layer including fluoride or oxide of alkali metal or alkaline earth metal may be inserted between the cathode and the organic layer in a thickness of from 0.1 to 5 nm. The dielectric layer can be regarded as one kind of an electron injecting layer. The dielectric layer can be formed, for example, according to a vacuum deposition method, a sputtering method, an ion plating method, etc.

The thickness of a cathode can be optionally selected in accordance with the materials of the cathode, so that cannot be regulated unconditionally, but the thickness is generally from 10 nm to 5 µm or so, and is preferably from 50 nm to 1 µm.

A cathode may be transparent or opaque. A transparent cathode can be formed by forming a thin film of the materials of the cathode in a thickness of from 1 to 10 nm, and further stacking transparent conductive materials such as ITO and IZO.

(Protective Layer)

In the invention, an organic electroluminescent device may be completely protected with a protective layer.

It is sufficient for the materials to be contained in the protective layer to have a function capable of restraining the substances accelerating deterioration of elemental device, e.g., water, oxygen, etc., from entering the device.

The specific examples of such materials include metals, e.g., In, Sn, Pb, Au, Cu, Ag, Al, Ti, Ni, etc., metal oxides, e.g., MgO, SiO, $SiO_2$, $Al_2O_3$, GeO, NiO, CaO, BaO, $Fe_2O_3$, $Y_2O_3$, $TiO_2$, etc., metal nitrides, e.g., $SiN_X$, $SiN_xO_y$, etc., metal fluorides, e.g., $MgF_2$, LiF, $AlF_3$, $CaF_2$, etc., polyethylene, polypropylene, polymethyl methacrylate, polyimide, polyurea, polytetrafluoroethylene, polychlorotrifluoroethylene, polydichlorodifluoroethylene, copolymers of chlorotrifluoroethylene with dichlorodifluoroethylene, copolymers obtained by copolymerization of a monomer mixture containing tetrafluoroethylene and at least one comonomer, fluorine-containing copolymers having a cyclic structure on the main chain of the copolymer, water absorptive substances having a water absorption rate of not lower than 1%, and moisture proofing substances having a water absorption rate of not higher than 0.1%.

The forming method of the protective layer is not especially restricted and, for example, a vacuum deposition method, a sputtering method, a reactive sputtering method, an MBE (molecular beam epitaxy) method, a cluster ion beam method, an ion plating method, a plasma polymerization method (a high frequency excitation ion plating method), a plasma CVD method, a laser CVD method, a heat CVD method, a gas source CVD method, a coating method, a printing method, a transfer method, etc., can be applied to the invention.

(Sealing Container)

An organic electroluminescent device of the invention may be completely sealed in a sealing container.

Further, a water absorber or an inert liquid may be filled in the space between the sealing container and the light-emitting device. The water absorber is not especially restricted and, for example, barium oxide, sodium oxide, potassium oxide, calcium oxide, sodium sulfate, calcium sulfate, magnesium sulfate, phosphorus pentoxide, calcium chloride, magnesium chloride, copper chloride, cesium fluoride, niobium fluoride, calcium bromide, vanadium bromide, molecular sieve, zeolite, magnesium oxide, etc., can be exemplified. The inert liquid is not particularly limited and, for example, paraffins, liquid paraffins, fluorine solvents, such as perfluoroalkane, perfluoroamine, perfluoroether, etc., chlorine solvents, and silicone oils are exemplified.

Luminescence can be obtained by the application of DC (if necessary, an alternating current factor may be contained) voltage (generally from 2 to 15 V) or DC electric current between the anode and cathode of a device of the invention.

In connection with the driving methods of a device of the invention, the driving methods disclosed in JP-A-2-148687, JP-A-6-301355, JP-A-5-29080, JP-A-7-134558, JP-A-8-234685, JP-A-8-241047, Japanese Patent No. 2784615, and. U.S. Pat. No. 5,828,429 and U.S. Pat. No. 6,023,308 can be used.

The external quantum efficiency of an light-emitting device of the invention is preferably 5% or more, more preferably 10% or more, and still more preferably 13% or more.

As the value of external quantum efficiency, the maximum value of the external quantum efficiency at the time of driving a device at 20° C., or the value of the external quantum efficiency near 100 to 300 cd/m$^2$ at the time of driving an elemental device at 20° C. can be used.

The inner quantum efficiency of a light-emitting device of the invention is preferably 30% or more, more preferably 50% or more, and still more preferably 70% or more. The inner quantum efficiency of a device is computed by dividing the external quantum efficiency by the efficiency of taking out light. In ordinary organic electroluminescent devices, the efficiency of taking out light is about 20%, but it is possible to make the efficiency of taking out light 20% or more by various contrivances such as the shape of a substrate, the shape of electrodes, the thickness of an organic layer, the thickness of an inorganic layer, the refractive index of an organic layer, and the refractive index of an inorganic layer.

In view of blue color purity, the light emitted from an organic electroluminescent device of the invention has a maximum wavelength of preferably from 390 to 495 nm, more preferably from 400 to 490 nm. Also, the light emitted from a light-emitting device of the invention may have another maximum wavelength at 500 nm or more, or an organic electroluminescent device of the invention may be a white light-emitting device.

In view of blue color purity, the x chromaticity value according to CIE of the light emitted from an organic electroluminescent device of the invention is preferably 0.22 or less, more preferably 0.20 or less.

In view of blue color purity, the y chromaticity value according to CIE of the light emitted from an organic electroluminescent device of the invention is preferably 0.25 or less, more preferably 0.20 or less.

In view of blue color purity, the half-value width of spectrum of the light emitted from an organic electroluminescent device of the invention is preferably 100 nm or less, more preferably 90 nm or less, still more preferably 80 nm or less, particularly preferably 70 nm or less.

EXAMPLES

<Synthesis of Compound (5-1)>

Compound 8-1 below is synthesized by reference to the technique described in literature (Tetrahedron Lett., 2003, 44, 1959). Specifically, iodine (2.5 g, 10 mmol) is added to a mixture of indole (11.72 g, 100 mmol), acetone (3.67 mL, 50 mmol), and acetonitrile (100 mL) at room temperature, followed by stirring the mixture for 3 hours. To the thus-obtained reaction solution is added an aqueous solution of sodium thiosulfate to discontinue the reaction. The reaction mixture is extracted with ethyl acetate, and the thus-obtained organic layer is dried over sodium sulfate, and concentrated. The residue is purified by silica gel column chromatography to obtain compound (8-1) (3.30 g, 12.0 mmol, 24%).

t-Butylphosphine (0.24 mL, 1.0 mmol) is added to a mixture of compound (8-1) (3.30 g, 12 mmol), bromobenzene (3.05 g, 29 mmol), palladium acetate (45 mg, 0.25 mmol), sodium t-butoxide (3.6 g, 36 mmol), and xylene (120 mL) in an atmosphere of nitrogen, followed by stirring the mixture for 1 hour under reflux. The thus-obtained reaction solution is cooled, water is added thereto, and the mixture is extracted with ethyl acetate. The combined organic layer is dried over sodium sulfate and, after concentrating the layer, the concentrate is purified by column chromatography. The thus-obtained solid is recrystallized from isopropyl alcohol. Filtration of the resulting solid product gives compound (5-1) (1.4 g). $^1$H NMR data of compound (5-1): δ=7.46-7.57 (m, 12H), 7.29-7.37 (m, 2H), 7.27 (s, 2H), 7.12 (dd, 2H), 6.96 (dd., 2H), 2.00 (s, 6H) in CDCl$_3$.

cooled, water is added thereto, and the mixture is extracted with ethyl acetate. The combined organic layer is dried over sodium sulfate and, after concentrating the layer, the concentrate is purified by column chromatography. The thus-obtained solid is dissolved in a heated ethyl acetate, and isopropyl alcohol is added thereto. The solid product precipitated is collected by filtration to obtain compound (5-2) (4.0 g).

$^1$H NMR data of compound (5-2): δ=2.60 (s, 3H), 7.00 (dd, 3H), 7.13 (s, 3H), 7.14 (dd, 3H), 7.26-7.32 (m, 3H), 7.41-7.48 (m, 12H), 7.55 (d, 3H), 7.64 (d, 3H), 300MHz in CDCl$_3$.

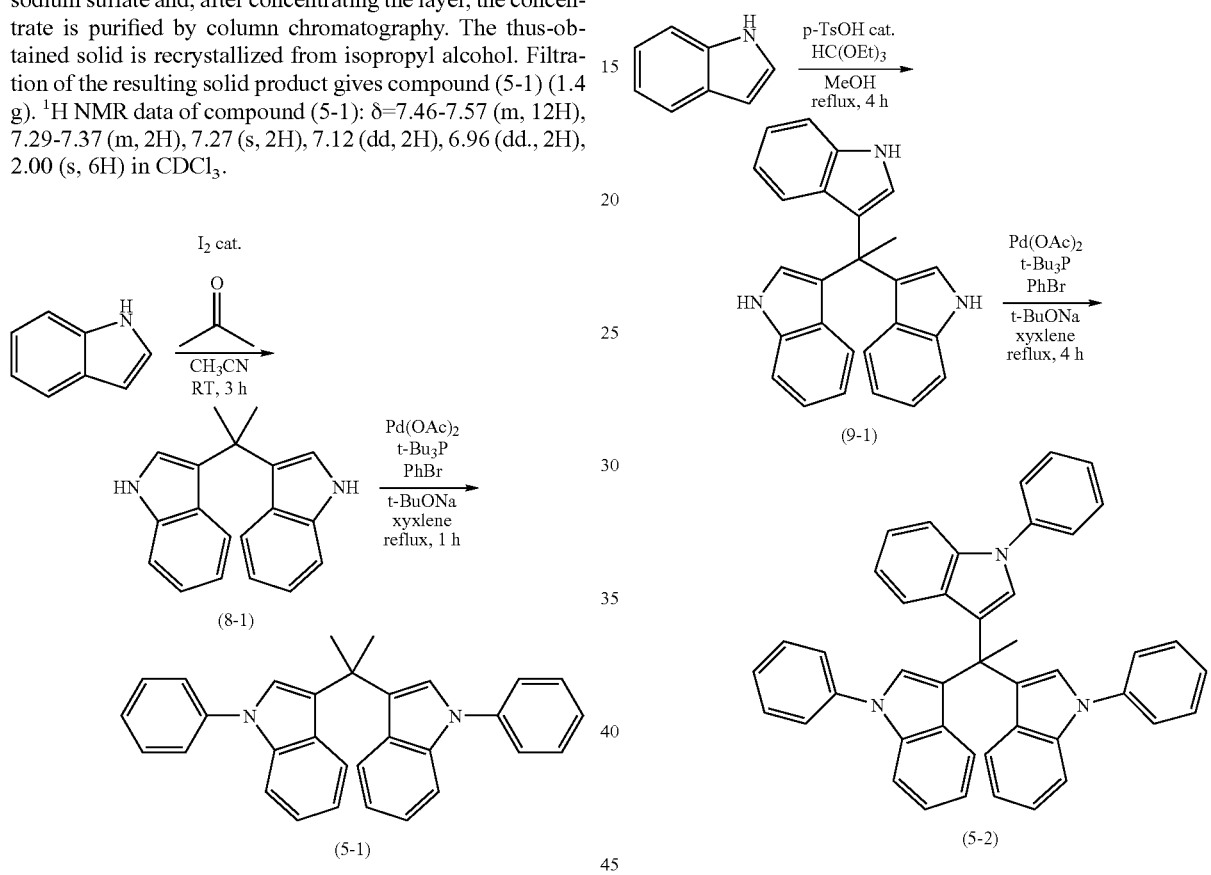

<Synthesis of Compound (5-2)>

Compound (9-1 below is synthesized by reference to the technique described in literature (J. Heterocyclic Chem., 1983, 20, 1303). Specifically, p-toluenesulfonic acid (0.05 g) is added to a methanol solution (100 mL) of a mixture of indole (23.4 g, 200 mmol) and triethyl orthoformate (13.4 mL, 73 mmol) in an atmosphere of nitrogen at room temperature, and the mixture is stirred for 4 hours under reflux. The thus-obtained reaction solution is air-cooled, and concentrated by an evaporator. A saturated sodium bicarbonate aqueous solution (100 mL) is added to the residue, and the mixture is extracted with ethyl acetate (50 mL, 3 times). The organic layers are combined, dried over sodium sulfate, and concentrated. The residue is purified by silica gel column chromatography to obtain compound (9-1) (15.0 g, 39.9 mmol, 60%).

t-Butylphosphine (0.60 mL, 2.4 mmol) is added to a mixture of compound (9-1) (7.51 g, 20 mmol), bromobenzene (6.64 mL, 63 mmol), palladium acetate (135 mg, 0.6 mmol), sodium t-butoxide (8.65 g, 90 mmol), and xylene (200 mL) in an atmosphere of nitrogen, followed by stirring the mixture for 4 hour under reflux. The thus-obtained reaction solution is <Synthesis of Compound (5-4)>

N-Phenylindole (4.78 g, 24.7 mmol) and N,N,N',N'-tetramethylethylenediamine (5.21 g, 44.8 mmol) are dissolved in 120 ml of n-hexane. To this mixture is gradually added dropwise a solution of tert-butyllithium (1.57 M) (23.5 ml, 36.9 mmol) under cooling with ice in an atmosphere of nitrogen, followed by stirring at 0° C. for 50 minutes. Thereafter, this mixture is cooled to −78° C., and diphenyldichlorosilane (2.84 g, 11.2 mmol) is gradually added dropwise thereto. After stirring at −78° C. for 2 hours and then at room temperature for further 2 hours, 200 ml of water is added thereto. This mixture is extracted with ethyl acetate (100 ml×3 times), and the recovered organic layer is washed with a saturated sodium chloride aqueous solution (50 ml× once). This organic layer is dried over magnesium sulfate (5 g), and the solvent is distilled off by means of a rotary evaporator. Thereafter, the residue is subjected to flash column chromatography using a hexane/ethyl acetate (30/1) mixed solvent, then to heat-washing using a hexane/ethyl acetate (30/1) mixed solvent to obtain a white powdery solid product of compound (5-4) (yield: 1.54 g; yield ratio: 24.3%).

¹H NMR data of compound (5-4): δ=7.60-7.65 (dd, 2H), 7.23-7.31 (m, 64H), 6.87-7.19 (m-22H), 300 MHz in CDCl₃.
<Synthesis of Compound (10-1)>
Compound (10-1) below is synthesized by reference to the technique described in JP-A-2002-305084.

Compound (10-1)

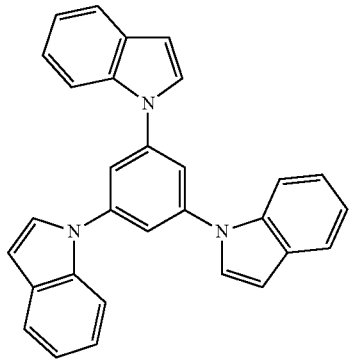

Comparative Example 1

A washed ITO substrate is placed in a vacuum deposition apparatus, and copper phthalocyanine is vacuum deposited thereon in a thickness of 10 nm, then NPD (N,N'-di-α-naphthyl-N,N'diphenyl)-benzidine) is vacuum deposited thereon in a thickness of 40 nm. An iridium complex (11-1) (light-emitting material) and compound (10-1) (host material) are vacuum deposited thereon in a thickness of 20 nm with a ratio of 10:90 (by weight) to form a light-emitting layer. BAlq (bis(2-methyl-8-quinolinolato-N1,O8)-(1,1'-biphenyl-4-olato)aluminum is vacuum deposited thereon in a thickness of 6 nm, then Alq (tris(8-hydroxyquinoline)aluminum complex is vacuum deposited thereon in a thickness of 20 nm. After vacuum depositing thereon lithium fluoride in a thickness of 3 nm, a 60-nm thick Al is provided thereon as a cathode by patterning using a shadow mask.

Each layer is provided by resistance heating vacuum deposition.

The thus-prepared layered material is placed in a globe box purged with a nitrogen gas, and is sealed up using a stainless steel-made seal can and a UV-curable adhesive (XNR5516HV manufactured by Nagase-Ciba).

When a direct current, a direct current constant voltage is applied to the organic electroluminescent device by means of a source measure unit Model 2400 manufactured by Toyo Corporation to emit light, there is obtained phosphorescent light emission derived from the iridium complex (11-1).

Comparative Example 2, Examples 1 to 4

Devices are prepared in the same manner as in Comparative Example 1 except for changing the light-emitting layer (co-vacuum deposited layer of the iridium complex (11-1) and the compound (10-1) to the constitutions shown in Table 1, and are allowed to emit light in the same manner as in Comparative Example 1. Thus, there are obtained phosphorescent light emission or fluorescent light emission derived from respective light-emitting materials.

Comparative Example 5

A device is prepared in the same manner as in Comparative Example 1 except for changing the formulation of the light-emitting layer to a formulation that the ratio of rubrene (dopant) to the compound (10-1) (host material) is 1:99 (by weight), and is allowed to emit light. Thus, there is obtained fluorescent light emission derived from rubrene.

Comparative Examples 6 to 8, Examples 7 to 10

Devices are prepared in the same manner as in Comparative Example 5 except for changing constitution of the light-emitting layer in Comparative Example 5 to that shown in Table 1, and are allowed to emit light. Thus, there are obtained fluorescent light emission derived from the respective light-emitting materials.

Results on the characteristic properties of the devices obtained in Comparative Examples and Examples 1 are tabulated in Table 1 below.

The devices are driven at 20 °C. and luminance of 360 cd/m² by the application of constant current, and the external quantum efficiency in each device is computed, as the luminance efficiency, from the obtained emission spectrum and front luminance by a luminance conversion method. The luminance efficiency and driving voltage are values obtained when driven at 360 cd/m². The time to half-luminance is a time till the initial luminance of 360 cd/cm² is reduced to a half level when driven at a constant electric current. Additionally, luminance is measured by using a luminance meter BM-8 (trade name) manufactured by Topcon.

TABLE 1

Characteristic properties of devices of the invention

| | | Time to | | Constitution of Light-emitting layer | |
| --- | --- | --- | --- | --- | --- |
| | Efficiency | Half-luminance | Driving Voltage | Dopant | Host material |
| Comparative Example 1 | 1.0 | 1.0 | 1.0 | (11-1) | (10-1) |
| Comparative Example 2 | 0.7 | 0.7 | 0.9 | (11-4) | (10-1) |
| Comparative Example 3 | 0.6 | 1.2 | 1.2 | D-10 | (10-1) |
| Comparative Example 4 | 0.8 | 1.1 | 1.0 | D-35 | (10-1) |
| Example 1 | 2.1 | 2.0 | 0.8 | (11-1) | (5-1) |
| Example 2 | 1.5 | 4.0 | 0.9 | (11-3) | (5-2) |
| Example 3 | 1.3 | 2.0 | 0.8 | (11-4) | (5-4) |
| Example 4 | 2.4 | 9.0 | 0.9 | (11-2) | (5-1) |
| Example 5 | 1.3 | 1.5 | 0.8 | D-10 | (5-1) |
| Example 6 | 2.3 | 11.0 | 0.7 | D-35 | (5-1) |
| Example 7 | 2.0 | 10.0 | 0.7 | (11-3) | (5-4) |
| Example 8 | 2.6 | 8.0 | 0.7 | D-35 | (5-4) |
| Example 9 | 2.4 | 12.0 | 0.7 | (11-3) | (5-1) |
| Comparative Example 5 | 0.3 | 1.2 | 0.8 | rubrene | (10-1) |
| Comparative Example 6 | 0.2 | 1.3 | 0.7 | Co-6 | (10-1) |
| Comparative Example 7 | 0.3 | 0.9 | 0.7 | perylene A | (10-1) |
| Comparative Example 8 | 0.3 | 0.7 | 0.8 | DCJT | (10-1) |
| Example 10 | 0.5 | 2.2 | 0.5 | Rubrene | (5-1) |
| Example 11 | 0.6 | 2.8 | 0.4 | Co-6 | (5-1) |
| Example 12 | 0.4 | 3.1 | 0.4 | perylene A | (5-1) |
| Example 13 | 0.5 | 1.8 | 0.5 | DCJT | (5-1) |

All the values shown in Table 1 are relative values based on the value of Comparative Example 1.

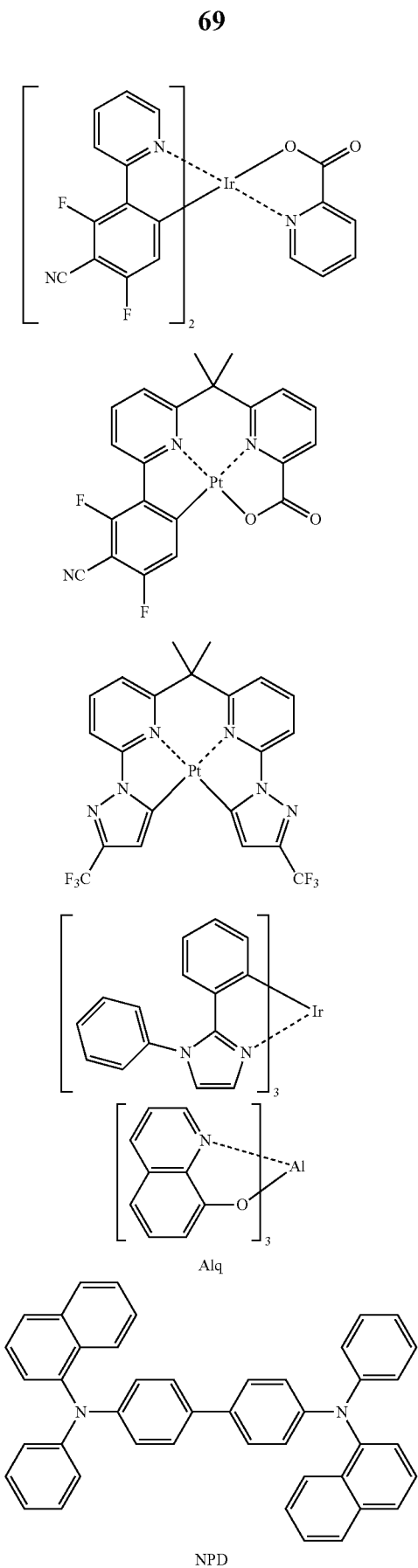

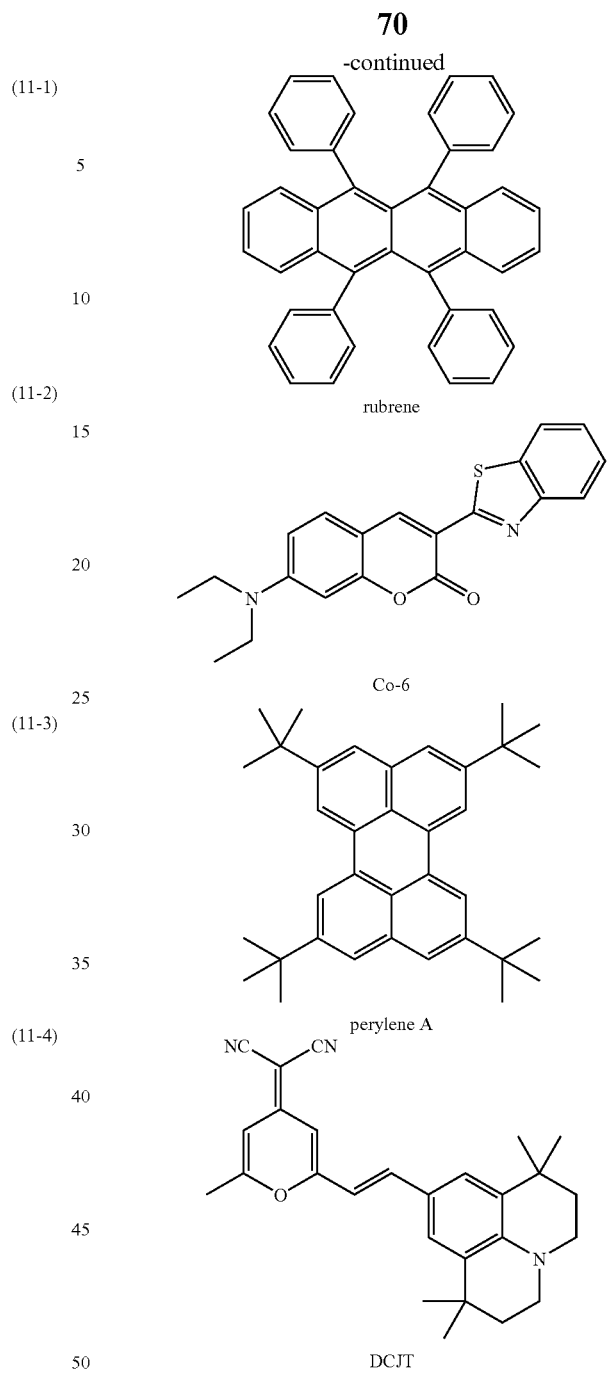

It is seen from Table 1 that, in comparison with the devices of Comparative Examples, the devices of the invention show excellent results with respect to light-emitting efficiency, luminance half time, and driving voltage. That is, the indole compounds in accordance with the invention wherein indole rings are connected to each other at 2- or 3-position of each indole ring show more excellent light-emitting efficiency, luminance half time, and driving voltage than the indole compounds wherein indole rings are connected to each other at 1-position thereof.

In addition, with devices prepared by using indole compounds in accordance with the invention other than the indole compounds shown in Table 1 as a host material, there are obtained more excellent results than in Comparative Examples as is the same with the results described above.

Further, as can be seen in Examples 2, 4, and 6 to 9, there are obtained the results that a combination of each indole compound in accordance with the invention and the platinum complex light-emitting material is particularly preferred.

It will be apparent to those skilled in the art that various modifications and variations can be made to the described embodiments of the invention without departing from the spirit or scope of the invention. Thus, it is intended that the invention cover all modifications and variations of this invention consistent with the scope of the appended claims and their equivalents.

The present application claims foreign priority based on Japanese Patent Application Nos. JP2007-94373 filed Mar. 30, 2007, the contents of which are incorporated herein by reference.

The invention claimed is:

1. An organic electroluminescent device comprising:
a pair of electrodes; and
at least one organic layer between the pair of electrodes, the at least one organic layer including a light-emitting layer,
wherein the at least one organic layer contains an indole compound represented by formula (3):

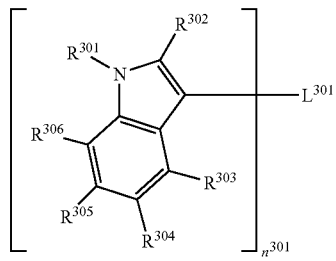

wherein $R^{301}$ represents an aryl group or a hetero ring group, $R^{302}$ to $R^{306}$ each represents a hydrogen atom, $L^{301}$ represents a substituted carbon atom where an alkyl group or aryl group is connected to the carbon atom, and $n^{301}$ represents an integer of 2 or 3.

2. The organic electroluminescent device according to claim 1, wherein $R^{301}$ is an aryl group.

3. The organic electroluminescent device according to claim 1, wherein the at least one organic layer contains a platinum complex having a tetradentate ligand.

4. The organic electroluminescent device according to claim 3, wherein the platinum complex is a compound represented by one of formulae (A), (C) and (D):

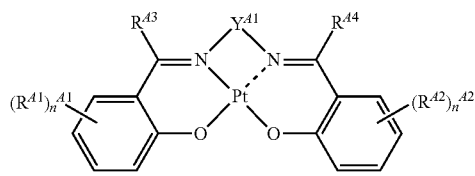

wherein $R^{A3}$ and $R^{A4}$ each independently represents a hydrogen atom, an aryl group or a heterocyclic group; and $R^{A1}$ and $R^{A2}$ each independently represents an aryl group or a heterocyclic group, and a plurality of $R^{A1}$s and $R^{A2}$s are present, the plurality of $R^{A1}$s and $R^{A2}$s may be the same or different and may be connected to each other to form a ring; $n^{A1}$ and $n^{A2}$ each independently represents an integer of from 0 to 4; and $Y^{A1}$ represents a linking group selected from the group consisting of an alkylene group, an arylene group, a hetero arylene group, an imino group, an oxy group, a thio group, a phosphinidene group, and a silylene group,

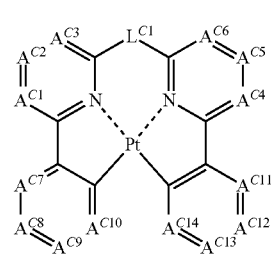

wherein $A^{C1}$ to $A^{C6}$ each independently represents C—R, Rs may be connected to form a ring, R in each of $A^{C2}$ and $A^{C5}$ is a hydrogen atom, an alkyl group, an aryl group, an amino group, an alkoxy group, an aryloxy group, a fluorine atom or a cyano group, R in each of $A^{C1}$, $A^{C3}$, $A^{C4}$, and $A^{C6}$ is a hydrogen atom, an alkyl group, an aryl group, an amino group, an alkoxy group, an aryloxy group, a fluorine atom or a cyano group, $A^{C7}$ to $A^{C14}$ each independently represents C—R or N, R in each of $A^{C8}$ and $A^{C12}$ is a hydrogen atom, an alkyl group, a polyfluoroalkyl group, an aryl group, an amino group, an alkoxy group, an aryloxy group, a fluorine atom or a cyano group, R in each of $A^{C7}$, $A^{C9}$, $A^{C11}$, and $A^{C13}$ is a hydrogen atom, an alkyl group, a polyfluoroalkyl group, an aryl group, an amino group, an alkoxy group, an aryloxy group, a fluorine atom or a cyano group, and R in each of $A^{C10}$ and $A^{C14}$ is a hydrogen atom or a fluorine atom; and $L^{C1}$ represents a single bond or a divalent linking group selected from the group consisting of an alkylene group, an arylene group and an imino group, and

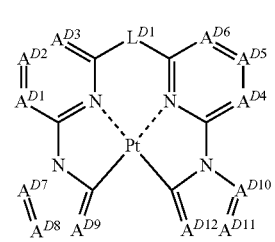

wherein $A^{D1}$ to $A^{D6}$ each independently represents C—R, Rs may be connected to form a ring, R in each of $A^{D2}$ and $A^{D5}$ is a hydrogen atom, an alkyl group, an aryl group, an amino group, an alkoxy group, an aryloxy group, a fluorine atom or a cyano group, R in each of $A^{D1}$, $A^{D3}$, $A^{D4}$, and $A^{D6}$ is a hydrogen atom, an alkyl group, an aryl group, an amino group, an alkoxy group, an aryloxy group, a fluorine atom or a cyano group, $A^{D7}$ to $A^{D12}$ each independently represents C—R or N, R in each of $A^{D8}$ and $A^{D11}$ is a hydrogen atom, an alkyl group, a polyfluoroalkyl group, an aryl group, an amino group, an alkoxy group, an aryloxy group, a fluorine atom or a cyano group, and R in each of $A^{D7}$, $A^{D9}$, $A^{10}$, and $A^{D12}$ is a hydrogen atom, an alkyl group, a polyfluoroalkyl group, an aryl group, an amino group, an alkoxy group, an aryloxy group, a fluorine atom or a cyano group; and $L^{D1}$ represents a single bond or a divalent linking group selected from the group consisting of an alkylene group, an arylene group and an imino group.

5. The organic electroluminescent device according to claim 1, wherein the light-emitting layer contains at least one indole compound represented by formula (3).

6. The organic electroluminescent device according to claim 1, wherein the at least one organic layer includes an electron transporting layer containing a metal complex material.

7. An indole compound represented by formula (4):

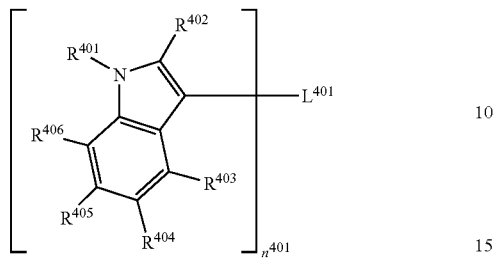

wherein $R^{401}$ represents an aryl group or a hetero ring group, R402 to $R^{406}$ each represents a hydrogen atom, $L^{401}$ represents a substituted carbon atom where an alkyl group or aryl group is connected to the carbon atom, and $n^{401}$ represents an integer of 2 or 3;

wherein the substituted or unsubstituted atom represented by $L^{401}$ is selected from the group consisting of a carbon atom, a silicon atom, a boron atom (in the case where $n^{401} \leq 3$), a nitrogen atom (in the case where $n^{401} \leq 3$), a phosphorus atom (in the case where $n^{401} \leq 3$), an oxygen atom (in the case where $n^{401} = 2$), and a sulfur atom (in the case where $n^{401} = 2$), and wherein the substituent for the substituted atom represented by $L^{401}$ is selected from the group consisting of an alkyl group, an aryl group, a heterocyclic group, a silyl group, and a halogen atom.

* * * * *